United States Patent
Nakayama et al.

[11] Patent Number: 5,885,990
[45] Date of Patent: Mar. 23, 1999

[54] SUBSTITUTED AMIDINONAPHTHYL ESTER DERIVATIVE

[75] Inventors: Toyoo Nakayama, Funabashi; Hiroyuki Kawamura, Ichikawa; Hiroyuki Uchiyama, Chiba, all of Japan

[73] Assignee: Torii Pharmaceutical Co., Ltd., Tokyo, Japan

[21] Appl. No.: 849,761

[22] PCT Filed: Dec. 27, 1995

[86] PCT No.: PCT/JP95/02723

§ 371 Date: Jun. 12, 1997

§ 102(e) Date: Jun. 12, 1997

[87] PCT Pub. No.: WO96/20917

PCT Pub. Date: Jul. 11, 1996

[30] Foreign Application Priority Data

Jan. 5, 1995 [JP] Japan ................................. 7-000242

[51] Int. Cl.⁶ ...................... C07D 277/18; C07D 295/14; C07D 233/24; C07C 257/18; C07C 279/18; A61K 31/245

[52] U.S. Cl. ..................... 514/238.5; 514/239.5; 514/319; 514/370; 514/426; 514/408; 514/510; 548/194; 548/331.5; 548/557; 548/569; 546/206; 544/162; 564/167; 562/440; 560/49; 560/20; 560/34; 560/35

[58] Field of Search ................................. 548/194, 331.5, 548/557, 569; 546/206; 544/162; 560/49, 20, 35, 34; 564/167; 562/440; 514/370, 398, 239.5, 238.5, 319, 426, 408, 510

[56] References Cited

FOREIGN PATENT DOCUMENTS

| 048433 A2 | 3/1982 | European Pat. Off. . |
| 0190356 A1 | 6/1986 | European Pat. Off. . |
| 57-53454 | 3/1982 | Japan . |
| 57-179146 | 4/1982 | Japan . |
| 61-3373 A | 2/1986 | Japan . |

OTHER PUBLICATIONS

Aoyama et al. (CA 104:19396, abstract of Chem. Pharm. Bull. (1985), 33(4), 1458–71).
*Chemical Pharmaceutical Bulletin*, vol. 33, No. 4 (1985), Takuo Aoyama, et al. "Synthesis and structure–activity study of protease inhibitors. IV. Amidinonaphthols and related acyl derivatives.", pp. 1458–1471.

Primary Examiner—S. Mark Clardy
Assistant Examiner—Sabiha N. Qazi
Attorney, Agent, or Firm—Beveridge, DeGrandi, Weilacher & Young, LLP

[57] ABSTRACT

Substituted amidinonaphthyl ester compounds effective for treatment of thrombosis are represented by the following formula (I) and pharmaceutically acceptable acid addition salts thereof:

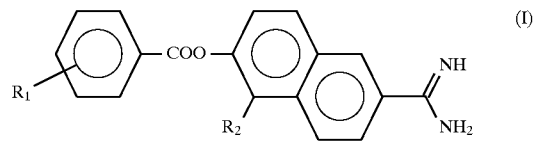

wherein $R_1$ represents (4,5-dihydro-1H-imidazol-2-yl) amino group, (4,5-dihydro-1,3-thiazol-2-yl)amino group, amidino group, morpholinomethyl group, nitro group, amino group, dimethylamino group,

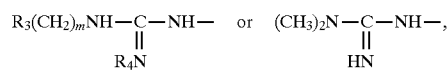

$R_3$ represents hydrogen, methoxy group, hydroxyl group, acetylamino group, morpholino group, piperidino group, 1-pyrrolidinyl group or dimethylamino group,
m represents 0–4,
$R_4$ represents hydrogen or methyl group,
$R_2$ represents $NH_2CO(CH_2)_n$—, 2-(carbamoyl)vinyl group or $R_5OOC(CH_2)_n$—,
$R_5$ represents dimethylcarbamoylmethyl group, hydrogen or lower alkyl group, and
n represents 0–2.

12 Claims, No Drawings

SUBSTITUTED AMIDINONAPHTHYL ESTER DERIVATIVE

This application has been filed under 35 USC 371 as a national stage application of PCT/JP95/02723 filed Dec. 27, 1995.

INDUSTRIAL FIELD OF THE INVENTION

The present invention relates to substituted amidinonaphthyl ester derivatives and pharmaceutical compositions containing the same as an active ingredient. The present invention further relates to intermediates for producing the said derivatives.

PRIOR ART

A clot formed in the heart or blood vessels due to coagulation of blood is called thrombus, and state of disease caused by the formation of thrombus is called thrombosis. Thrombosis includes various diseases such as cerebral infarction, myocardial infarction, pulmonary infarction and the like.

The methods for treatment of thrombosis is roughly classified into two methods from the point of action. That is, one is anti-thrombotic method which inhibits formation of thrombus and another is thrombolysis method according to which the formed thrombi are resolved.

It is considered that according to the thrombolysis method, plasminogen which is a precursor of fibrinolysis regulatory factor is activated into plasmin by giving a thrombolysis and this plasmin decomposes fibrin which forms thrombi in blood vessel whereby thrombi are resolved to open occluded parts. Medicines used for the thrombolysis method include, for example, tissue plasminogen activators (t-PA) which are plasminogen activators activating plasminogen into plasmin, substances in living body such as urokinase (UK) and the like, substances produced by cells such as staphylokinase, streptokinase and the like, and recombinants thereof.

Problems to be Solved by the Invention

However, the above t-PA and others are generally considered to be effective when intravenously administered. Since they are short in half-life in blood and rapidly removed from liver and, furthermore, inhibitors are present in living bodies, they must be administered in a large dosage to develop the thrombolysis action at the part where thrombi have been produced. The high dosage of the thrombus resolvent given in a short time is expected to markedly enhance the thrombus-resolving action systemically and open the occluded parts, and, on the other hand, it has been reported that it causes serious bleeding. Moreover, it has been reported as a result of animal experiments and clinical trials that even if the occluded parts are temporarily opened by the administration of the thrombolytic agents, the parts are apt to be reoccluded. This is a serious problem. Another problem in administration is that since the thrombolytic agents are injections, if they are administered for a long period of time, it gives a heavy burden to patients.

For the above reasons, development of medicines which have thrombolytic activity action and can be orally administered has been desired to reduce the burden for patients.

Means for Solving the Problems

The inventors have found that compounds represented by the following formula (I) have fibrinolysis promoting action and excellent thrombolysis action. As a result, the above problems have been solved and the present invention has been accomplished. That is, the present invention relates to a compound represented by the formula (I):

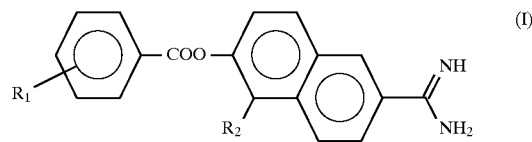

(wherein $R_1$ represents (4,5-dihydro-1H-imidazol-2-yl)amino group, (4,5-dihydro-1,3-thiazol-2-yl)amino group, amidino group, morpholinomethyl group, nitro group, amino group, dimethylamino group,

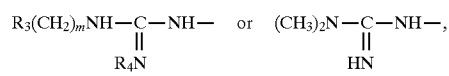

$R_3$ represents hydrogen, methoxy group, hydroxyl group, acetylamino group, morpholino group, piperidino group, 1-pyrrolidinyl group or dimethylamino group, m represents 0–4, $R_4$ represents hydrogen or methyl group, $R_2$ represents $NH_2CO(CH_2)_n-$, 2-(carbamoyl)vinyl group or $R_5OOC(CH_2)_n-$, $R_5$ represents dimethylcarbamoylmethyl group, hydrogen or lower alkyl group, and n represents 0–2).

The present invention further relates to pharmaceutical compositions containing the above compound (I).

Furthermore, the present invention relates to a compound represented by the formula (II) useful as an intermediate for the production of the compound (I):

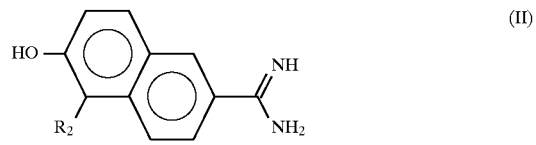

(wherein $R_2$ represents $NH_2CO(CH_2)_n-$, 2-(carbamoyl)vinyl group or $R_5OOC(CH_2)_n-$, $R_5$ represents dimethylcarbamoylmethyl group, hydrogen or lower alkyl group, and n represents 0–2, with a proviso that $R_5=CH_3$ and n=0 are excluded).

The present compound (1) has fibrinolysis promoting action and exhibits excellent thrombusresolving action and is effective for treatment of diseases caused by thrombus. That is, it can be used as medicines for general thrombosis and embolism, for example, medicines for treatment of thrombosis and embolism such as venous thrombosis, myocardial infarction, pulmonary occlusion, cerebral embolism, slowly advancing cerebral thrombosis, and thrombosis and embolism caused by operation of blood vessels and extracorporeal circulation, and improvement of obstruction of blood stream, improvement of various diseases caused by chronic artery occlusion, and treatment of thrombosis and embolism caused by ischemic cerebral artery injuries.

Representative processes for producing the present compound (I) and intermediate therefor are shown below.

Process for producing substituted amidinonaphthyl ester derivatives:

Scheme A

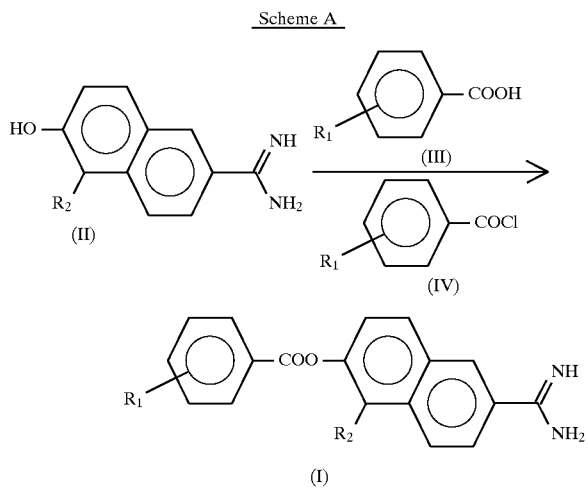

(wherein $R_1$ and $R_2$ are as defined above).

The present compound (I) can be produced by reacting a carboxylic acid derivative represented by the formula (III) or a reactive intermediate thereof with a substituted amidinonaphthol derivative represented by the formula (II) in the above Scheme A.

The reactive intermediate here means a reaction intermediate obtained by the reaction of the carboxylic acid derivative (III) with an acid halide (IV) used for general dehydration condensation, a mixed acid anhydride, N,N'-dicyclohexylcarbodiimide (DCC), 1-ethyl-3-(3-dimethylaminopropyl)-carbodiimide (EDC), diphenylphosphorylazide (DPPA) or the like which is generally used as a dehydration condensation agent.

The process for producing the present compound (I) will be explained in more detail.

The carboxylic acid derivative (III) is dissolved or suspended in an organic solvent such as N,N-dimethylformamide (DMF), N,N-dimethylacetamide (DMA), pyridine, a mixture thereof, or the like and is reacted with a carboxylic acid activator such as DCC, EDC, DPPA or the like. Then, the substituted aminodinaphthol derivative (II) is added, whereby the present compound (I) can be produced.

For example, when DCC is used as a dehydration condensation agent, the carboxylic acid derivative (III) is dissolved or suspended in a suitable solvent such as anhydrous or hydrous pyridine or the like, and the substituted amidinonaphthol derivative (II) is added thereto, followed by stirring under cooling or heating. After completion of the reaction, dicyclohexylurea (DCU) in the reaction mixture is removed, followed by carrying out usual treatments, whereby the present compound (I) can be produced. If necessary, the product is further purified by silica gel column chromatography.

When acid halide (IV) is used, the carboxylic acid derivative (III) is reacted with an acid halogenating agent such as thionyl chloride, thionyl bromide, phosphorus pentachloride or the like to obtain an acid halide derivative. Thereto is added the substituted amidinonaphthol derivative (II), whereby the present compound (I) can be produced. As the reaction solvent, DMF, DMA, dimethyl sulfoxide (DMSO), pyridine or the like is used and the reaction is effected using a dehydrohalogenating agent under cooling or heating. As the dehydrohalogenating agent, can be used inorganic bases such as potassium carbonate, sodium carbonate, sodium hydroxide and the like and organic bases such as triethylamine, pyridine, dimethylaniline and the like.

When the terminal functional group of $R_2$ is a carboxylic acid, the corresponding amide or lower alkyl ester is treated with an inorganic acid such as hydrochloric acid, sulfuric acid or the like or an organic acid such as methanesulfonic acid, ethanesulfonic acid or the like under heating, whereby the present compound (I) can be produced.

The thus obtained present compound (I) can be converted to the corresponding acid addition salt by usual salt exchanging method. Any acids can be used as far as the salts are usable as medicines, and examples of the acids are inorganic acids such as hydrochloric acid, hydrobromic acid, sulfuric acid, phosphoric acid and the like and organic acids such as acetic acid, lactic acid, citric acid, methanesulfonic acid, ethanesulfonic acid, toluenesulfonic acid, succinic acid, fumaric acid, maleic acid and the like.

Process for the production of substituted amidinonaphthol derivative:

Substituted amidinonaphthol derivative (II) is a compound useful as an intermediate for producing the present compound (I).

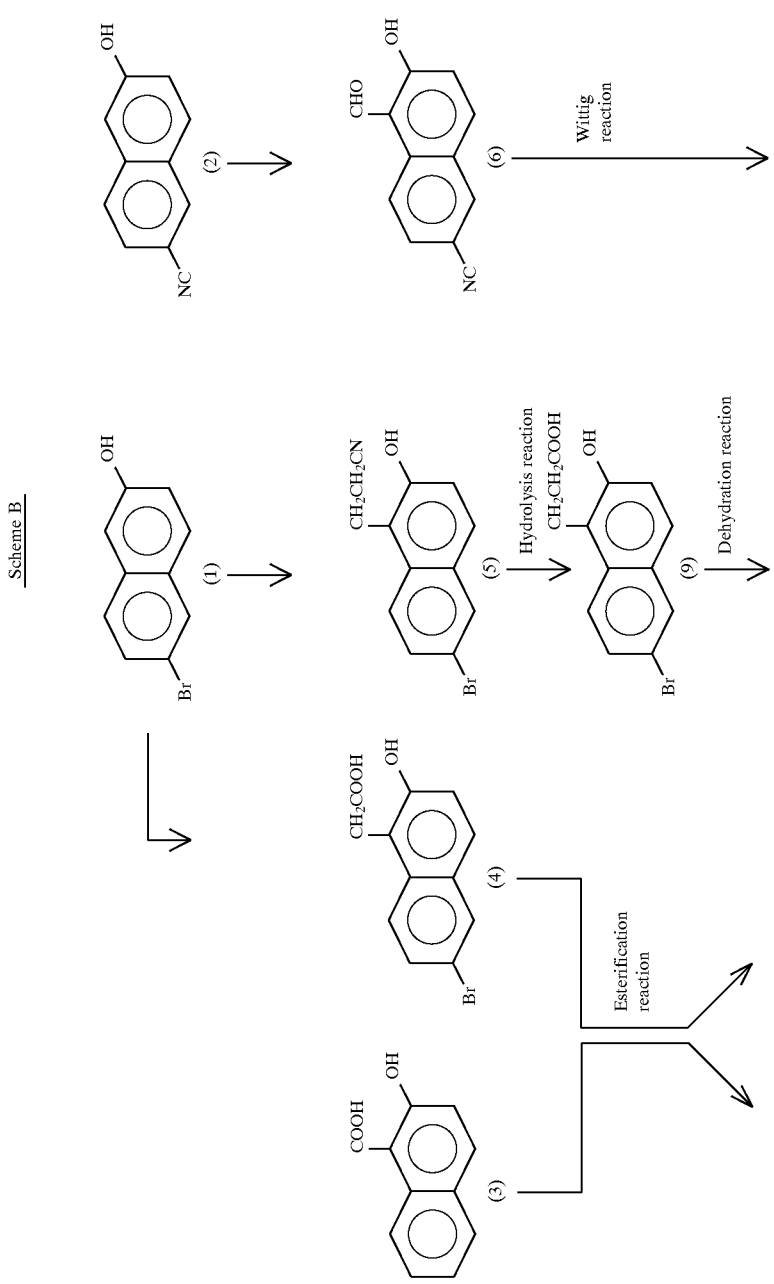

-continued
Scheme B
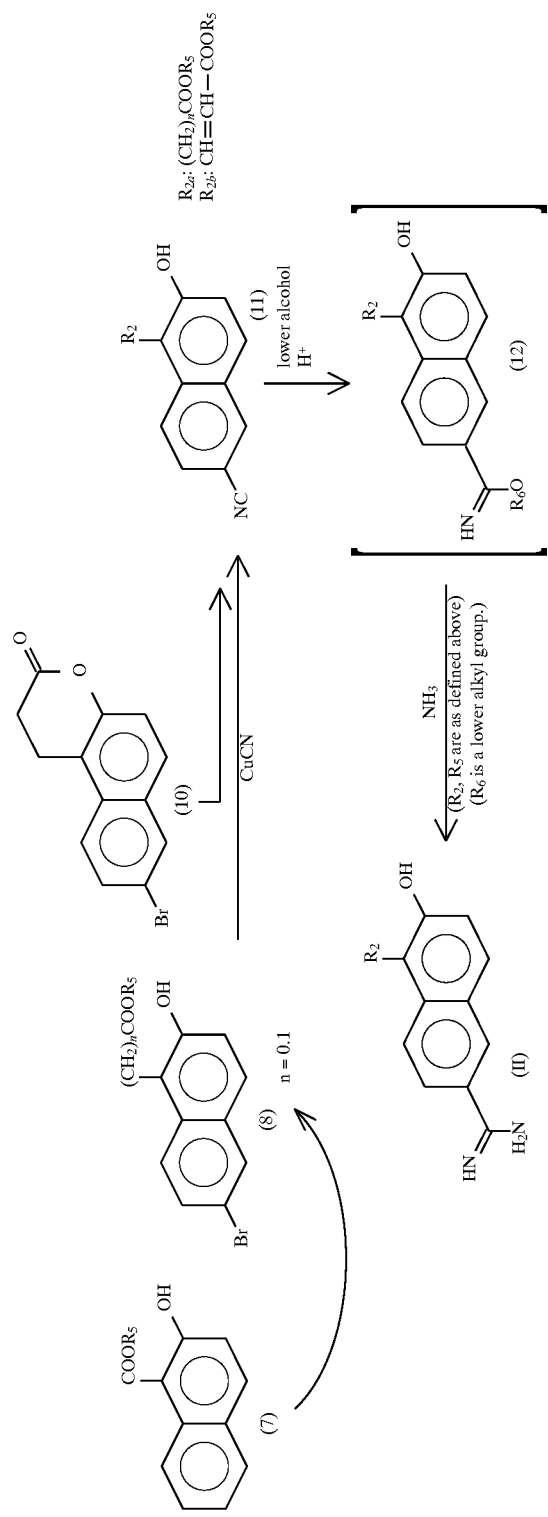

The substituted amidinonaphthol derivative (II) can be produced by various synthesis reactions as shown in Scheme B using known compounds (1), (2), (3) and (4) as starting materials. That is, ester (8) can be produced by esterification of compounds (3) and (4) using various lower alcohols or halogenated alkyls or bromination of compound (7).

Lactone compound (10) can be produced by the process of A. F. Hardman et al (J. Am. Chem. Soc., 70, 2119(1984)) from compound (1) through cyanoethyl compound (5) and carboxylic acid compound (9).

Nitrile (11)-$R_{2a}$ can be produced by reacting copper cyanide with compounds (8) and (10) in accordance with the process of Friedman et al (J. Org. Chem., 26, 2522(1961)). Nitrile (11)-R2b can be produced by formylating compound (2) using paraformaldehyde or the like to yield compound (6) and subjecting the compound (6) to the Wittig reaction using phospholan.

Substituted amidinonaphthol derivative (II) can be produced through imidate (12) in accordance with the Pinner process. The imidate (12) is produced by reacting the nitrile (11) with an equal or much excess amount of a lower alcohol in the presence of a hydrogen halide such as hydrogen chloride or hydrogen bromide under cooling or heating, and the imidate is further reacted with ammonia in a solvent such as a lower alcohol, N,N-dimethylformamide, dimethyl sulfoxide or the like under cooling or heating, whereby the substituted amidinonaphthol derivative (II) can be produced.

The present compound can be administered to mammals (including human patients) in the form of oral dosage or rectal dosage in view of its pharmacological action.

Furthermore, the present compound can be administered as one medicine or mixtures with other medicines. They can be administered as single compound or compounds, but are generally administered in the form of pharmaceutical composition. Examples of the composition are tablet, powder, capsule, syrup, and aqueous solution. For the oral compositions, there may be used ordinary additives such as excipient, lubricant, disintegrator, wetting agent and the like. Oral liquid formulation may be in the form of aqueous or oil suspension, solution, emulsion, syrup, elixir or the like, or it may be used as a dry syrup which is reprepared with water or other appropriate solvents before use. The liquid formulation can contain usual additives such as suspending agent, perfume, diluent and emulsifying agent.

In the case of rectal administration, the composition can be administered as a suppository. The suppository is prepared using appropriate bases such as cacao butter, laurin butter, Macrogol, glycero gelatin, Witepsol, sodium stearate or mixtures thereof and, if necessary, with addition of emulsifying agent, suspending agent, preservative and the like.

Examples of the excipient and others used in the compositions are enumerated below.

Excipient: Calcium hydrogenphosphate, synthetic aluminum silicate, magnesium metasilicate aluminate, aluminum-magnesium hydroxide, magnesium silicate, calcium carbonate, magnesium carbonate, calcium hydrogenphosphate, precipitated silicic acid anhydride, silicic acid anhydride, Avicel, various starches, dextrin, carboxymethyl starch (CMS), lactose.

Binder: Ethylcellulose (EC), sodium carboxymethylcellulose (CMC-Na), low-substitution hydroxypropylcellulose (L-HPC), hydroxypropylmethylcellulose (HPMC), methylcellulose (MC), hydroxypropylcellulose (HPC), various starches, dextrin, sodium alginate, gelatin, polyvinyl alcohol (PVA), polyvinyl pyrrolidone (PVP).

Disintegrator: Synthetic aluminum silicate, magnesium metasilicate aluminate, CMC-Ca, CMC, Avicel, L-HPC, HPMC, MC, various starches, CMS, hydroxypropyl starch (CPS).

Solidification inhibitor: Precipitated silicic acid anhydride, synthetic aluminum silicate.

Lubricant: Synthetic aluminum silicate, silicic acid anhydride, talc, Avicel.

Corrigent: Mannitol, citric acid, sodium citrate, sugar.

Emulsifying agent: Gelatin, citric acid, sodium citrate, polyoxyethylene hardened castor oil, Macrogol (PEG), propylene glycol fatty acid esters, polyoxyethylenepolyoxypropylene glycol, propylene glycol, sodium laurylsulfate, phospholipid.

Stabilizing agent: Sodium hydrogensulfite, polyoxyethylene hardened castor oil, PEG, propylene glycol fatty acid esters, polyoxyethylenepolyoxypropylene glycol, propylene glycol, sodium laurylsulfate, various natural and synthetic cyclodextrins, phospholipid.

Absorption promotor: Polyoxyethylene hardened castor oil, PEG, propylene glycol fatty acid esters, polyoxyethylenepolyoxypropylene glycol, propylene glycol, sodium laurylsulfate, various natural and synthetic cyclodextrins, middle-chain fatty acid triglycerides.

Solubilizing agent: Ethanol, polyoxyethylene hardened castor oil, PEG, propylene glycol fatty acid esters, polyoxyethylenepolyoxypropylene glycol, propylene glycol, sodium laurylsulfate, various natural and synthetic cyclodextrins.

Suspending agent: CMC-Na, HPMC, MC, HPC, sodium alginate, gelatin, propylene glycol, sodium laurylsulfate.

Coating agent: EC, magnesium silicate, talc, titanium oxide, calcium carbonate, triacetin, carboxymethylethylcellulose (CMEC), cellulose acetate phthalate (CAP), HPMC, hydroxypropylmethylcellulose phthalate (HPMCP), MC, HPC, sodium alginate, polyvinyl acetal diethylaminoacetate, sodium polyacrylate, copolymers of various acrylic acid and methacrylic acid derivatives, sodium polyglycolate.

Coloring agent: Titanium oxide, tar dye, caramel.

Dosage of the present compound when orally administered to human is 100–1000 mg/day, preferably 300–900 mg/day, more preferably 400–800 mg/day. However, when it is administered to human for curative purpose, the dosage is suitably adjusted depending on degree of seriousness of disease, age, body weight and the like.

The present invention will be explained more specifically by the following examples and formulation examples, which never limit the invention.

EXAMPLE 1

Preparation of 6-amidino-1-carbamoylmethyl-2-naphthyl 4-[(4,5-dihydro-1H-imidazol-2-yl)amino]-benzoate.dihydrochloride:

45 Milliliters of 20% hydrous pyridine was added to 2.85 g of 4-[(4,5-dihydro-1H-imidazol-2-yl)amino]benzoic acid.hydrochloride, 3 g of 6-amidino-1-carbamoylmethyl-2-naphthol.hydrochloride, 2.65 g of N,N'-dicyclohexylcarbodiimide (hereinafter referred to as "DCC") and 131 mg of 4-dimethylaminopyridine (hereinafter referred to as "DMAP"), followed by stirring for 2 hours under cooling with ice and 3 days under cooling with water. The precipitate was filtered and the filtrate was concentrated under reduced pressure. To the residue was added 15 ml of N,N-dimethylformamide (hereinafter referred to as "DMF"), and a small amount of the insoluble matter was filtered off. The filtrate was added dropwise to 500 ml of a mixed liquid of ether and acetone (10:1) and this was stirred for 24 hours under cooling with ice. Then, the precipitate was collected by filtration to obtain a crude product.

Then, the product was subjected to silica gel column chromatography using methyl ethyl ketone-water-acetic acid (80:15:5) as an eluent, and the desired fractions were collected and the solvent was distilled off under reduced pressure. The residue was dissolved in 10 ml of methanol and 3.6 ml of 6N hydrochloric acid, and the solution was added dropwise to 400 ml of a mixed liquid of ether and acetone (3:1) under cooling with ice. After stirring for 3 hours, the precipitate was collected by filtration to obtain 963 mg of the desired product.

$^1$H-NMR (DMSO-$d_6$) δ ppm:

| | |
|---|---|
| 11.74 (1H, S) | 7.64 (1H, d, J = 8.9 Hz) |
| 9.72 (2H, S) | 7.54 (2H, d, J = 8.9 Hz) |
| 9.52 (2H, S) | 7.03 (1H, S) |
| 8.80 (2H, S) | 3.99 (2H, S) |
| 8.67 (1H, S) | 3.73 (4H, S) |
| 8.31 (1H, d, J = 8.9 Hz) | 8.22 (2H, d, J = 8.6 Hz) |
| 8.09 (1H, d, J = 9.2 Hz) | 7.96 (1H, d, J = 8.9 Hz) |
| 7.73 (1H, S) | |

Reference Example 1

Preparation of methyl 2-hydroxy-6-bromo-1-naphthylacetate:

126.5 Grams of 2-hydroxy-6-bromo-1-naphthylacetic acid, 700 ml of methanol and 2 ml of concentrated sulfuric acid were stirred at room temperature for 24 hours. Then, the reaction mixture was concentrated under reduced pressure. The precipitate was collected by filtration and washed with small amounts of methanol and water to obtain 125.5 g of the desired product.

$^1$H-NMR (DMSO-$d_6$) δ ppm:

| | |
|---|---|
| 10.01 (1H, S) | 6.93–8.36 (5H, m) |
| 4.04 (2H, S) | 3.59 (3H, S) |

Reference Example 2

Preparation of 2-hydroxy-6-cyano-1-naphthylacetic acid:

100 Milliliters of DMF was added to 177 g of methyl 2-hydroxy-6-bromo-1-naphthylacetate and 70.9 g of cuprous cyanide, and refluxed under heating for 3.5 hours in a nitrogen stream. With stirring under heating, 300 ml of water was added and supernatant liquid was decanted, and then this procedure was repeated. To the resulting residue was added 2.3 liters of a 4% aqueous sodium hydroxide solution, followed by stirring at 25° C. for 1 hour. The insoluble matter was filtered, and concentrated hydrochloric acid was added to the filtrate and the precipitate was collected by filtration. To this collected precipitate was added 200 ml of water, and thereto were added 501 g of ferrous sulfate.heptahydrate and 60 ml of concentrated hydrochloric acid, followed by stirring at 70° C. for 1 hour. After leaving for cooling, the resulting precipitate was collected by filtration and sufficiently washed with water. Thereafter, 3 liters of methanol was added thereto to dissolve the precipitate at 40° C. The insoluble matter was filtered off, and 3 liters of water was added to the filtrate to obtain a crude product. The product was repeatedly subjected to recrystallization with 10% hydrous methanol to obtain 42 g of the desired product.

$^1$H-NMR (DMSO-$d_6$) δ ppm:

| | |
|---|---|
| 12.23 (1H, br) | 10.50 (1H, br) |
| 7.03–8.82 (5H, m) | 3.99 (2H, S) |

Reference Example 3

Preparation of methyl 2-hydroxy-6-cyano-1-naphthylacetate:

A solution containing 18.2 g of 2-hydroxy-6-cyano-1-naphthylacetic acid, 250 ml of methanol and 3 g of methanesulfonic acid was stirred at 40° C. to perform dissolution, followed by stirring at room temperature for 2 days. Then, 5 g of active carbon was added, followed by stirring for 30 minutes. Thereafter, the insoluble matter was filtered off and the solvent was distilled off under reduced pressure. To the residue was added 50 ml of 50% hydrous methanol, and then the precipitate was collected by filtration to obtain 13 g of the desired product.

$^1$H-NMR (DMSO-$d_6$) δ ppm:

| | |
|---|---|
| 10.49 (1H, S) | 8.41 (1H, S) |
| 7.49–8.22 (3H, m) | 7.34 (1H, d, J = 8.8 Hz) |
| 4.08 (2H, S) | 3.61 (3H, S) |

EXAMPLE 2

Preparation of 6-amidino-1-carbamoylmethyl-2-naphthol.hydrochloride:

1.2 Liter of anhydrous methanol was added to 58 g of methyl 2-hydroxy-6-cyano-1-naphthylacetate, and the solution was saturated with hydrogen chloride gas under cooling with ice, followed by stirring at 50° C. for 24 hours. The precipitate was collected by filtration and washed with a small amount of ether. To the collected precipitate was added 3.1 liters of anhydrous methanol, and ammonia gas was passed therethrough under cooling with water and stirring to dissolve the precipitate, followed by stirring for 4 days at the same temperature. The precipitate was collected by filtration and washed with a small amount of methanol. To this collected precipitate was added 730 ml of water, and 240 ml of concentrated hydrochloric acid was added under cooling with ice, followed by stirring for 30 minutes. Then, the precipitate was collected by filtration and washed with 250 ml of acetone to obtain 44.2 g of the desired product.

$^1$H-NMR (DMSO-$d_6$) δ ppm:

| | |
|---|---|
| 10.63 (1H, S) | 3.90 (2H, S) |
| 8.84–10.15 (4H, br) | 6.48–8.81 (7H, m) |

EXAMPLE 3

Preparation of 6-amidino-1-carbamoylmethyl-2-naphthyl 4-[(2-acetylaminoethyl)iminomethylaminomethylamino]benzoate.dihydrochloride:

20 Milliliters of 20% hydrous pyridine was added to 1.4 g of 4-[(2-acetylaminoethyl)iminomethylaminomethylamino]benzoic acid.hydrobromide, 1.0 g of 6-amidino-1-carbamoylmethyl-2-naphthol.hydrochloride, 884 mg of DCC and 43.6 mg of DMAP, followed by stirring for 2 hours under cooling with ice and 4 days at room temperature. The precipitate was filtered and the filtrate was added dropwise to 250 ml of a mixed liquid of ether and acetone (1:10) and this was stirred for 24 hours under cooling with ice. Then, the precipitate was collected by filtration. To this collected precipitate was added 7 ml of DMF to dissolve the precipitate with heating, and 1.46 ml of concentrated hydrochloric acid was added under cooling with ice and stirring. This solution was added dropwise to 400 ml of ether.acetone (1:20), followed by stirring for 1 hour under cooling with ice and then 24 hours under cooling with water. After the supernatant was decanted, 20 ml of DMF was again added to the residue to dissolve the residue with heating, and further 1.5 ml of concentrated hydrochloric acid was added under cooling with water and stirring. This solution was added dropwise to 400 ml of acetone, followed by stirring for 1 hour under cooling with ice and then 24 hours under cooling with water. Thereafter, the precipitate was collected by filtration to obtain a crude product.

Then, the product was subjected to silica gel column chromatography using a mixed liquid of methyl ethyl ketone-water-acetic acid (80:15:5) as an eluent, and the desired fractions were collected and the solvent was distilled off under reduced pressure. The residue was dissolved in 8 ml of DMF and 1 ml of concentrated hydrochloric acid, and the solution was added dropwise to 200 ml of acetone under cooling with ice. After stirring for 1 hour under cooling with ice and then 24 hours under cooling with water, the precipitate was collected by filtration to obtain 939.2 mg of the desired product.

$^1$H-NMR (DMSO-$d_6$) δ ppm:

| | |
|---|---|
| 10.44 (1H, S) | 7.78 (1H, S) |
| 9.75 (2H, S) | 7.71 (1H, d, J = 8.9 Hz) |
| 9.53 (2H, S) | 7.60 (2H, d, J = 8.9 Hz) |
| 8.73 (1H, S) | 7.12 (1H, S) |
| 8.46 (2–3H, br) | 4.06 (2H, S) |
| 8.38 (1H, d, J = 8.9 Hz) | 3.52 (2H, brs) |
| 8.28 (2H, d, J = 8.9 Hz) | 3.25–3.47 (2H, m) |
| 8.18 (1H, d, J = 9.2 Hz) | 3.00 (3H, S) |
| 7.94–8.14 (2H, m) | 1.99 (3H, S) |

Reference Example 4

Preparation of 2-hydroxy-6-bromo-1-(2-cyanoethyl) naphthalene:

To 44.8 g of 6-bromo-2-naphthol were added 120 ml of toluene and 8.8 g of sodium hydroxide, followed by stirring at 65° C. for 30 minutes. Then, thereto was added dropwise 11.4 g of acrylonitrile at 80° C., followed by stirring at the same temperature for 3.5 hours. After left for cooling, the toluene layer was decanted, and to the residue was added 240 ml of water. A small amount of insoluble matter was filtered off, and to the filtrate was added 140 ml of 5% hydrochloric acid. The precipitate was collected by filtration and sufficiently washed with water. The resulting crude product was recrystallized from ethanol to obtain 30.7 g of the desired product.

$^1$H-NMR (DMSO-$d_6$) δ ppm:

| | |
|---|---|
| 10.05 (1H, S) | 7.03–8.26 (5H, m) |
| 2.33–3.62 (4H, m) | |

Reference Example 5

Preparation of 3-(2-hydroxy-6-bromo-1-naphthyl) propionic acid:

To 27.6 g of 2-hydroxy-6-bromo-1-(2-cyanoethyl) naphthalene was added 88 g of 10% sodium hydroxide, followed by refluxing for 7 hours under heating. After the mixture was left for cooling, it was made acidic with dilute hydrochloric acid, and then the precipitate was collected by filtration and washed with water. To the collected precipitate was added 1.2 liter of water, and furthermore 168 g of sodium hydrogencarbonate was added with stirring to dissolve the precipitate. Then, a small amount of insoluble matter was filtered off, and concentrated hydrochloric acid was added to the filtrate to render the filtrate acidic. Then, the precipitate was collected by filtration and washed with water to obtain 17.3 g of the desired product.

$^1$H-NMR (DMSO-$d_6$) δ ppm:

| | |
|---|---|
| 9.86–11.66 (2H, brs) | 6.71–8.28 (5H, m) |
| 2.08–3.44 (4H, m) | |

Reference Example 6

Preparation of 4-bromobenzo[1,2-f]-3,4-dihydrocoumarin:

30 Milliliters of toluene was added to 5.9 g of 3-(2-hydroxy-6-bromo-1-naphthyl)propionic acid, followed by refluxing with heating for 5.5 hours. After the mixture was left for cooling, 20 ml of cyclohexane was added, followed by stirring for 30 minutes, and thereafter the precipitate was collected by filtration to obtain 5.1 g of the desired product.

$^1$H-NMR (DMSO-$d_6$) δ ppm:

| | |
|---|---|
| 7.04–8.44 (5H, m) | 2.64–3.65 (4H, m) |

Reference Example 7

Preparation of methyl 3-(2-hydroxy-6-cyano-1-naphthyl) propionate:

To 83.1 g of 4-bromobanzo[1,2-f]-3,4-dihydrocoumarin were added 200 ml of DMF and 33.1 g of cuprous cyanide, and the mixture was stirred at 140°–145° C. for 7 hours in a nitrogen stream. After left for cooling for 24 hours, 280 ml of DMF was added and the insoluble matter was filtered off, followed by washing with 2.5 liters of methanol four times. The filtrate and the wash liquid were combined and insoluble matter was filtered off. To the filtrate was added 16 liters of water, followed by stirring for 24 hours, and the precipitate was collected by filtration and washed with water. Then, the collected precipitate was dissolved in 2.1 liters of acetone, and, thereafter, a small amount of insoluble matter was filtered off. To the filtrate was added 16 liters of water, followed by stirring for 2 hours. Then, the precipitate was collected by filtration and washed with water to obtain 34.5 g of the desired product.

$^1$H-NMR (DMSO-$d_6$) δ ppm:

| | |
|---|---|
| 10.34 (1H, S) | 7.04–8.67 (5H, m) |
| 3.60 (3H, S) | 2.96–3.53 (2H, m) |
| 2.25–2.79 (2H, m) | |

EXAMPLE 4

Preparation of 2-hydroxy-6-amidino-1-(2-carbamoylethyl)naphthalene.hydrochloride:

34.5 Grams of methyl 3-(2-hydroxy-6-cyano-1-naphthyl) propionate was slowly added to 360 ml of anhydrous methanol solution saturated with hydrogen chloride gas with stirring under cooling with ice, followed by further stirring for 24 hours under cooling with water. Then, hydrogen chloride gas was passed therethrough for 2 hours, followed by further stirring for 48 hours. The precipitate was collected by filtration and washed with a small amount of acetone. The collected precipitate was slowly added to 960 ml of anhydrous methanol saturated with ammonia gas with stirring under cooling with ice, followed by further stirring for 48 hours at room temperature. The precipitate was collected by filtration and washed with a small amount of acetone. Then, the precipitate was added to 60 ml of water. With stirring at room temperature, 10% hydrochloric acid was added dropwise little by little to render the solution acidic, followed by stirring for 2.5 hours. The precipitate was collected by filtration and washed with a small amount of acetone to obtain 26.1 g of the desired product.

$^1$H-NMR (DMSO-$d_6$) δ ppm:

| | |
|---|---|
| 9.44 (4H, brs) | 8.46 (1H, S) |
| 8.11 (1H, d, J = 9.2 Hz) | 7.69–7.98 (2H, m) |
| 7.50 (1H, S) | 7.41 (1H, d, J = 8.9 Hz) |
| 6.91 (1H, S) | 3.02–3.36 (2H, m) |
| 3.02–3.36 (2H, m) | 2.21–2.48 (2H, m) |

EXAMPLE 5

Preparation of 6-amidino-1-(2-carbamoylethyl)-2-naphthyl 4-[(4,5-dihydro-1H-imidazol-2-yl)amino]-benzoate.dihydrochloride:

45 Milliliters of 20% hydrous pyridine was added to 2.71 g of 4-[(4,5-dihydro-1H-imidazol-2-yl)amino]benzoic acid.hydrochloride, 3.0 g of 6-amidino-1-(2-carbamoylethyl)-2-naphthol.hydrochloride, 2.52 g of DCC and 124.6 mg of DMAP, followed by stirring for 2 hours under cooling with ice and 6 days under cooling with water. The precipitate was filtered and the filtrate was concentrated under reduced pressure. To the residue was added 15 ml of DMF, and a small amount of insoluble matter was filtered off. The filtrate was added dropwise to 400 ml of acetone, followed by stirring for 1 hour under cooling with ice and 24 hours under cooling with water. The supernatant was decanted, and to the residue was added 15 ml of methanol, followed by stirring for 1 hour under cooling with ice. The precipitate was collected by filtration to obtain a crude product. Then, the product was subjected to silica gel column chromatography using a mixed liquid of methyl ethyl ketone-water-acetic acid (80:15:5) as an eluent solvent, and the desired fractions were collected and the solvent was distilled off under reduced pressure. The residue was dissolved in 5 ml of DMF and 200 μl of concentrated hydrochloric acid, and the solution was added dropwise to 200 ml of acetone. After stirring for 1 hour under cooling with ice and then 24 hours under cooling with water, the precipitate was collected by filtration to obtain 495.4 mg of the desired product.

$^1$H-NMR (DMSO-$d_6$) δ ppm:

| | |
|---|---|
| 8.62 (1H, d, J = 2.0 Hz) | 8.42 (1H, d, J = 9.2 Hz) |
| 8.35 (2H, d, J = 8.6 Hz) | 8.18 (1H, d, J = 9.2 Hz) |
| 8.00 (1H, dd, J1 = 8.9, J2 = 1.7 Hz) | |
| 7.64 (1H, d, J = 8.9 Hz) | 7.56 (1H, d, J = 8.6 Hz) |
| 3.81 (4H, S) | 3.21–3.44 (2H, m) |
| 2.43–2.57 (2H, m) | |

EXAMPLE 6

Preparation of 6-amidino-1-carbamoylmethyl-2-naphthyl 3-[(4,5-dihydro-1H-imidazol-2-yl)amino]-benzoate.dihydrochloride:

15 Milliliters of 20% hydrous pyridine was added to 634.1 mg of 3-[(4,5-dihydro-1H-imidazol-2-yl)amino]benzoic acid.hydrochloride, 676.7 mg of 6-amidino-1-carbamoylmethyl-2-naphthol.hydrochloride, 598 mg of DCC and 29.5 mg of DMAP, followed by stirring for 2 hours under cooling with ice and then 24 hours under cooling with water. Thereafter, the same procedure as in Example 1 was carried out to obtain 439.5 mg of the desired product.

$^1$H-NMR (DMSO-$d_6$) δ ppm:

| | |
|---|---|
| 11.39 (1H, S) | 9.70 (2H, S) |
| 9.51 (2H, S) | 8.66 (2H, S) |
| 8.33 (1H, d, J = 8.9 Hz) | 7.90–8.17 (5H, m) |
| 7.54–7.86 (3H, m) | 7.03 (1H, S) |
| 4.03 (2H, S) | 3.70 (4H, S) |

EXAMPLE 7

Preparation of 6-amidino-1-carbamoylmethyl-2-naphthyl 4-[(2-hydroxyethyl)aminoiminomethylamino]-benzoate.dihydrochloride:

20 Milliliters of 20% hydrous pyridine was added to 1.02 g of 4-[(2-hydroxyethyl)aminoiminomethylamino]benzoic acid.hydrochloride, 1.0 g of 6-amidino-1-carbamoylmethyl-2-naphthol.hydrochloride, 884 mg of DCC and 43.6 mg of DMAP, followed by stirring for 2 hours under cooling with ice and then 24 hours at room temperature. Thereafter, the same procedure as in Example 1 was carried out to obtain 1.17 g of the desired product.

$^1$H-NMR (DMSO-$d_6$) δ ppm:

| | |
|---|---|
| 10.58 (1H, S) | 9.67 (2H, S) |
| 9.45 (2H, S) | 8.65 (1H, d, J = 1.7 Hz) |
| 8.42 (1H, brs) | 7.83–8.36 (8H, m) |
| 7.69 (1H, S) | 7.64 (1H, d, J = 8.9 Hz) |
| 7.49 (2H, d, J = 8.6 Hz, m) | |
| 7.03 (1H, S) | 3.98 (2H, S) |
| 3.53–3.63 (2H, m) | 3.29–3.51 (2H, m) |

EXAMPLE 8

Preparation of 6-amidino-1-carbamoylmethyl-2-naphthyl 4-morpholinomethylbenzoate.dihydrochloride:

15 Milliliters of anhydrous pyridine was added to 612.2 mg of 4-morpholinomethylbenzoic acid, 703.9 mg of 6-amidino-1-carbamoylmethyl-2-naphthol.hydrochloride, 622.6 mg of DCC and 30.7 mg of DMAP, followed by stirring for 2 hours under cooling with ice and then 3 days under cooling with water. Thereafter, the same procedure as in Example 1 was carried out to obtain 440.7 mg of the desired product.

¹H-NMR (DMSO-d₆) δ ppm:

| | |
|---|---|
| 12.15 (1H, S) | 9.66 (2H, S) |
| 9.46 (2H, S) | 8.64 (1H, S) |
| 8.22–8.52 (3H, m) | 8.11 (1H, d, J = 8.9 Hz) |
| 7.87–8.04 (3H, m) | 7.48–7.80 (2H, m) |
| 7.02 (1H, S) | 4.49 (2H, S) |
| 4.00 (2H, S) | 3.94 (4H, S) |
| 3.08–3.36 (4H, m) | |

EXAMPLE 9

Preparation of 6-amidino-1-(2-carbamoylethyl)-2-naphthyl 4-[(2-hydroxyethyl)aminoiminomethylamino]-benzoate.dihydrochloride:

20 Milliliters of 20% hydrous pyridine was added to 1.45 g of 4-[(2-hydroxyethyl)aminoiminomethylamino]benzoic acid.hydrochloride, 1.5 g of 6-amidino-1-(2-carbamoylethyl)-2-naphthol.hydrochloric acid, 1.26 g of DCC and 62.3 mg of DMAP, followed by stirring for 2 hours under cooling with ice and then 24 hours at room temperature. Thereafter, the same procedure as in Example 1 was effected to obtain 1.17 g of the desired product.

¹H-NMR (DMSO-d₆) δ ppm:

| | |
|---|---|
| 10.59 (1H, S) | 9.70 (2H, S) |
| 9.48 (2H, S) | 8.68 (1H, S) |
| 7.84–8.52 (7H, m) | 7.60 (1H, d, J = 8.9 Hz) |
| 7.34–7.57 (3H, m) | 6.84 (1H, brs) |
| 3.55–3.69 (2H, m) | 3.36–3.52 (2H, m) |
| 3.13–3.34 (2H, m) | 2.29–2.48 (2H, m) |

EXAMPLE 10

Preparation of 6-amidino-1-carbamoylmethyl-2-naphthyl 4-guanidinobenzoate.hydrochloric acid methanesulfonate:

100 Milliliters of 20% hydrous pyridine was added to 3.0 g of 4-guanidinobenzoic acid.methanesulfonate, 3.0 g of 6-amidino-1-carbamoylmethyl-2-naphthol.hydrochloride and 4.5 g of DCC, followed by stirring for 2 hours under cooling with ice and then 2 days at room temperature. The precipitate was filtered and 1 g of active carbon was added to the filtrate, followed by stirring for 30 minutes under cooling with ice, and insoluble matter was filtered off. The filtrate was slowly added dropwise to 4 liters of ether under cooling with ice, followed by stirring for 2 hours. The precipitate was collected by filtration and washed with 100 ml of acetone to obtain a crude product. Then, the product was dissolved in 150 ml of methanol. Thereafter, 2.5 g of active carbon was added to the solution, followed by stirring for 30 minutes under cooling with ice, and insoluble matter was filtered off. The filtrate was slowly added dropwise to 1 liter of acetone under cooling with ice, followed by stirring for 2 hours. The precipitate was collected by filtration to obtain 2.9 g of the desired product.

¹H-NMR (DMSO-d₆) δ ppm:

| | |
|---|---|
| 9.48 (5H, brs) | 6.55–8.72 (15H, m) |
| 3.98 (2H, S) | 2.45 (3H, S) |

EXAMPLE 11

Preparation of 6-amidino-1-carbamoylmethyl-2-naphthyl 4-nitrobenzoate.hydrochloride:

30 Milliliters of anhydrous pyridine and 10 ml of DMF were added to 1.8 g of 4-nitrobenzoic acid, 3.0 g of 6-amidino-1-carbamoylmethyl-2-naphthol.hydrochloride, 2.7 g of DCC and 130.9 mg of DMAP, followed by stirring for 2 hours under cooling with ice and then 24 hours at room temperature. Then, the precipitate was collected by filtration and washed with a small amount of DMF. To this collected precipitate was added 100 ml of DMF, to dissolve the precipitate with heating, followed by stirring for 2 hours under cooling with ice. Then, insoluble matter was filtered off and the filtrate was concentrated to 20 ml under reduced pressure. The residue was added dropwise to 400 ml of acetone, followed by stirring for 24 hour under cooling with ice. The precipitate was collected by filtration to obtain a crude product. Then, the product was subjected to silica gel column chromatography using chloroformmethanol-acetic acid (80:15:5) as an eluent, and the desired fractions were collected and the solvent was distilled off under reduced pressure. The residue was suspended with addition of 20 ml of methanol and 0.6 ml of concentrated hydrochloric acid, and the suspension was added dropwise to a mixed liquid of 200 ml of ether and 20 ml of acetone, followed by stirring for 24 hours under cooling with ice. Then, the precipitate was collected by filtration to obtain 1.35 g of 6-amidino-1-carbamoylmethyl-2-naphthyl 4-nitrobenzoate.hydrochloride.

¹H-NMR (DMSO-d₆) δ ppm:

| | |
|---|---|
| 9.66 (2H, S) | |
| 7.96 (1H, dd, J1 = 8.9, J2 = 1.7 Hz) | |
| 9.45 (2H, S) | 7.71 (1H, d, J = 8.9 Hz) |
| 8.64 (1H, d, J = 1.7 Hz) | 7.70 (1H, S) |
| 8.45 (4H, S) | 7.01 (1H, S) |
| 8.36 (1H, d, J = 8.9 Hz) | 4.02 (2H, S) |
| 8.12 (1H, d, J = 8.9 Hz) | |

EXAMPLE 12

Preparation of 6-amidino-1-carbamoylmethyl-2-naphthyl 4-aminobenzoate.dihydrochloride;

To 600 mg of 6-amidino-1-carbamoylmethyl-2-naphthyl 4-nitrobenzoate.hydrochloride were added 10 ml of anhydrous DMF and 100 mg of 10% palladium carbon, and catalytic reduction was effected at room temperature for 24 hours. Then, insoluble matter was filtered off and the filtrate was concentrated under reduced pressure. To the residue was added 15 ml of methanol, and, furthermore, 350 μl of concentrated hydrochloric acid was added with stirring under cooling with ice. Then, the resulting solution was added dropwise to 200 ml of acetone, followed by stirring for 1 hour under cooling with ice. Then, the precipitate was collected by filtration to obtain 572.7 mg of the desired product.

¹H-NMR (DMSO-d₆) δ ppm:

| | |
|---|---|
| 9.64 (2H, S) | 7.58 (2H, d, J = 8.9 Hz) |
| 9.43 (2H, S) | 7.04 (3H, brs) |
| 8.62 (1H, d, J = 1.7 Hz) | 6.96 (1H, S) |
| 8.26 (1H, d, J = 8.9 Hz) | 6.91 (2H, d, J = 8.6 Hz) |
| 8.06 (1H, d, J = 8.9 Hz) | 3.95 (2H, S) |
| 7.83–8.03 (3H, m) | |

EXAMPLE 13

Preparation of 6-amidino-1-carbamoylmethyl-2-naphthyl 2-nitrobenzoate.hydrochloride:

50 Milliliters of anhydrous pyridine and 20 ml of DMF were added to 5.0 g of 2-nitrobenzoic acid, 3.0 g of 6-amidino-1-carbamoylmethyl-2-naphthol.hydrochloride, 4.4 g of DCC and 218.2 mg of DMAP, followed by stirring for 2 hours under cooling with ice and 24 hours at room temperature. Then, the precipitate was filtered and washed with 100 ml of warm DMF. This wash liquid and the filtrate were combined, and the solvent was distilled off under reduced pressure. To the residue was added 20 ml of DMF, and the resulting solution was added dropwise to 600 ml of acetone, followed by stirring for 2 hours under cooling with ice. Then, the precipitate was collected by filtration to obtain a crude product. Then, the product was subjected to silica gel column chromatography using chloroformmethanol-acetic acid (80:15:5) as an eluent, and the desired fractions were collected and the solvent was distilled off under reduced pressure. To ½ of the residue were added 20 ml of methanol and 1.4 ml of concentrated hydrochloric acid to suspend the residue. The suspension was added dropwise to a mixed liquid of 200 ml of ether and 200 ml of acetone, followed by stirring for 24 hours under cooling with ice. Then, the precipitate was collected by filtration to obtain 2.42 g of 6-amidino-1-carbamoylmethyl-2-naphthyl 2-nitrobenzoate.hydrochloride.

$^1$H-NMR (DMSO-$d_6$) δ ppm:

| | |
|---|---|
| 9.65 (2H, S) | 7.88–8.09 (3H, m) |
| 9.43 (2H, S) | 7.75 (1H, S) |
| 8.63 (1H, d, J = 1.7 Hz) | 7.66 (1H, d, J = 8.9 Hz) |
| 8.35 (1H, d, J = 8.9 Hz) | 7.08 (1H, S) |
| 8.10–8.30 (3H, m) | 4.02 (2H, S) |

EXAMPLE 14

Preparation of 6-amidino-1-carbamoylmethyl-2-naphthyl 2-aminobenzoate.hydrochloride:

To the other ½ of the residue in Example 13 was added 20 ml of methanol to suspend the residue, and the resulting suspension was added dropwise to a mixed liquid consisting of 150 ml of ether and 150 ml of acetone, followed by stirring for 24 hours under cooling with ice. Then, the precipitate was collected by filtration to obtain 1.80 g of 6-amidino-1-carbamoylmethyl-2-naphthyl 2-nitrobenzoate.acetate. To 1.0 g of 6-amidino-1-carbamoylmethyl-2-naphthyl 2-nitrobenzoate.acetate were added 50 ml of anhydrous DMF and 200 mg of 10% palladium carbon, and catalytic reduction was effected at room temperature for 24 hours. Then, insoluble matter was filtered off and the filtrate was concentrated under reduced pressure. To the residue was added 20 ml of methanol, and 0.6 ml of concentrated hydrochloric acid was added thereto under stirring and cooling with ice. Then, the resulting solution was added dropwise to 400 ml of acetone, followed by stirring for 24 hours under cooling with ice. Then, the precipitate was collected by filtration to obtain a crude product. Then, the product was subjected to silica gel column chromatography using chloroformmethanol-acetic acid (80:15:5) as an eluent, and the desired fractions were collected and the solvent was distilled off under reduced pressure. The residue was dissolved in 20 ml of methanol and 0.6 ml of concentrated hydrochloric acid, and the solution was added dropwise to 350 ml of acetone, followed by stirring for 24 hours under cooling with ice. Then, the precipitate was collected by filtration to obtain 344.6 mg of the desired product.

$^1$H-NMR (DMSO-$d_6$) δ ppm:

| | |
|---|---|
| 9.62 (2H, S) | 7.26–7.44 (1H, m) |
| 9.41 (2H, S) | 7.03 (1H, S) |
| 8.61 (1H, d, J=1.7 Hz) | 6.88 (1H, d, J=8.6 Hz) |
| 8.28 (1H, d, J=8.9 Hz) | 6.79 (2H, S) |
| 7.85–8.14 (3H, m) | 6.57–6.71 (1H, m) |
| 7.64 (1H, S) | 3.95 (2H, S) |
| 7.59 (1H, d, J=8.9 Hz) | |

EXAMPLE 15

Preparation of 6-amidino-1-carbamoylmethyl-2-naphthyl 4-dimethylaminobenzoate.dihydrochloride:

40 Milliliters of 20% hydrous pyridine was added to 3.0 g of 4-dimethylaminobenzoic acid, 1.77 g of 6-amidino-1-carbamoylmethyl-2-naphthol.hydrochloride, 2.65 g of DCC and 130.9 mg of DMAP, followed by stirring for 2 hours under cooling with ice and then 24 hours at room temperature. Then, the precipitate was collected by filtration and washed with a small amount of pyridine. To this collected precipitate were added 60 ml of DMF and 20 ml of water to dissolve the precipitate with heating, followed by stirring for 2 hours under cooling with ice. Then, insoluble matter was filtered off and the filtrate was concentrated under reduced pressure. To the residue were added 15 ml of DMF and 10 ml of water to dissolve the residue. The solution was added dropwise to 400 ml of acetone, followed by stirring for 24 hour under cooling with ice. The precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. The residue was suspended in 15 ml of methanol, 5 ml of DMF and 0.9 ml of concentrated hydrochloric acid, and the suspension was added dropwise to a mixed liquid of 200 ml of acetone and 100 ml of ether, followed by stirring for 24 hours under cooling with ice. Then, the precipitate was collected by filtration to obtain 1.96 g of the desired product.

$^1$H-NMR (DMSO-$d_6$) δ ppm:

| | |
|---|---|
| 9.67 (2H, S) | 7.63 (1H, brs) |
| 9.47 (2H, S) | 7.58 (1H, d, J=8.9 Hz) |
| 8.63 (1H, d, J=1.7 Hz) | 7.03 (1H, brs) |
| 8.25 (1H, d, J=8.9 Hz) | 6.85 (3H, d, J=9.2 Hz) |
| 8.06 (1H, d, J=8.9 Hz) | 3.94 (2H, S) |
| 8.00 (2H, d, J=9.2 Hz) | 3.06 (6H, S) |
| 7.95 (1H, dd, J=8.9, J2=1.7 Hz) | |

EXAMPLE 16

Preparation of 6-amidino-1-carbamoylmethyl-2-naphthyl 4-[(2-acetylaminoethyl)aminoiminomethylamino]-benzoate.dihydrochloride:

40 Milliliters of 10% hydrous pyridine was added to 1.5 g of 4-[(2-acetylaminoethyl)aminoiminomethylamino] benzoic acid.hydrochloride, 1.12 g of 6-amidino-1-carbamoylmethyl-2-naphthol.hydrochloride, 1.55 g of DCC and 61 mg of DMAP, followed by stirring for 2 hours under cooling with ice and then 48 hours at room temperature. The precipitate was filtered and the filtrate was concentrated under reduced pressure. To the residue was added 15 ml of methanol, and this solution was added dropwise to 400 ml of acetone, followed by stirring for 24 hour under cooling with ice. The precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 15 ml of methanol and 0.96 ml of concentrated hydrochloric acid, and the solution was added dropwise to 400 ml of acetone, followed by stirring for 24 hours under cooling with ice. Then, the precipitate was collected by filtration to obtain 1.24 g of the desired product.

$^1$H-NMR (DMSO-$d_6$) δ ppm:

| | |
|---|---|
| 10.60 (1H, S) | 7.69 (1H, S) |
| 9.65 (2H, S) | 7.64 (1H, d, J=8.9 Hz) |
| 9.43 (2H, S) | 7.49 (2H, d, J=8.6 Hz) |
| 8.64 (1H, d, J=1.7 Hz) | 7.04 (1H, S) |
| 8.47 (1H, brs) | 3.98 (2H, S) |
| 8.17–8.38 (5H, m) | 3.17–3.55 (4H, m) |
| 8.10 (1H, d, J=8.9 Hz) | 1.87 (3H, S) |
| 7.96 (1H, dd, J1=8.9, J2=1.7 Hz) | |

EXAMPLE 17

Preparation of 6-amidino-1-carbamoylmethyl-2-naphthyl 4-[(2-dimethylaminoethyl)aminoiminomethylamino]benzoate.trihydrochloride:

40 Milliliters of 20% hydrous pyridine was added to 1.5 g of 4-[(2-dimethylaminoethyl)aminoiminomethylamino]benzoic acid.dihydrochloride, 1.03 g of 6-amidino-1-carbamoylmethyl-2-naphthol.hydrochloride, 1.44 g of DCC and 56 mg of DMAP, followed by stirring for 2 hours under cooling with ice and then 24 hours at room temperature. The precipitate was filtered and the filtrate was concentrated under reduced pressure. To the residue was added 15 ml of methanol, and this solution was added dropwise to 400 ml of acetone, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 15 ml of methanol and 1.41 ml of concentrated hydrochloric acid, and the solution was added dropwise to 400 ml of acetone, followed by stirring for 24 hours under cooling with ice. Then, the precipitate was collected by filtration to obtain 1.52 g of the desired product.

$^1$H-NMR (DMSO-$d_6$) δ ppm:

| | |
|---|---|
| 10.97 (1H, brs) | |
| 7.97 (1H, dd, J1=8.9, J2=1.7 Hz) | |
| 10.80 (1H, S) | 7.72 (1H, S) |
| 9.678 (2H, S) | 7.64 (1H, d, J=8.9 Hz) |
| 9.46 (2H, S) | 7.54 (2H, d, J=8.6 Hz) |
| 8.65 (2H, d, J=1.7 Hz) | 7.04 (1H, S) |
| 8.49 (1H, brs) | 3.98 (2H, S) |
| 8.30 (1H, d, J=8.9 Hz) | 3.72–3.94 (2H, m) |
| 8.22 (2H, d, J=8.6 Hz) | 3.24–3.49 (2H, m) |
| 8.10 (1H, d, J=8.9 Hz) | 2.84 (6H, d, J=3.0 Hz) |

EXAMPLE 18

Preparation of 6-amidino-1-carbamoylmethyl-2-naphthyl 4-[(2-methoxyethyl)aminoiminomethylamino]-benzoate.dihydrochloride:

50 Milliliters of 10% hydrous pyridine was added to 1.5 g of 4-[(2-methoxyethyl)aminoiminomethylamino]benzoic acid.hydrochloride, 1.22 g of 6-amidino-1-carbamoylmethyl-2-naphthol.hydrochloride, 1.7 g of DCC and 67 mg of DMAP, followed by stirring for 2 hours under cooling with ice and then 24 hours at room temperature. The precipitate was filtered and the filtrate was concentrated under reduced pressure. To the residue was added 15 ml of ethanol and 15 ml of isopropanol, and the precipitate was collected by filtration. To the collected precipitate were added 15 ml of DMF and 1.34 ml of concentrated hydrochloric acid to dissolve the precipitate. Furthermore, 1 g of active carbon was added, followed by stirring for 2 hours at room temperature. The insoluble matter was filtered off and the filtrate was added dropwise to 400 ml of acetone, followed by stirring for 24 hour under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 15 ml of methanol and 1.34 ml of concentrated hydrochloric acid, and the solution was added dropwise to 400 ml of acetone, followed by stirring for 24 hours under cooling with ice. Then, the precipitate was collected by filtration to obtain 1.25 g of the desired product.

$^1$H-NMR (DMSO-$d_6$) δ ppm:

| | |
|---|---|
| 10.61 (1H, brs) | 7.64 (1H, d, J=8.9 Hz) |
| 9.67 (2H, S) | 7.47 (2H, d, J=8.6 Hz) |
| 9.45 (2H, S) | 7.04 (1H, S) |
| 8.65 (1H, d, J=1.7 Hz) | 3.98 (2H, S) |
| 8.48 (1H, brs) | 3.52 (4H, S) |
| 7.85–8.44 (7H, m) | 3.33 (3H, S) |
| 7.70 (1H, S) | |

EXAMPLE 19

Preparation of 6-amidino-1-carbamoylmethyl-2-naphthyl 4-(morpholinoaminoiminomethylamino)-benzoate.dihydrochloride:

55 Milliliters of 10% hydrous pyridine was added to 1.5 g of 4-morpholinoaminoiminomethylamino-benzoic acid.hydrochloride, 1.12 g of 6-amidino-1-carbamoylmethyl-2-naphthol.hydrochloride, 1.55 g of DCC and 61 mg of DMAP, followed by stirring for 2 hours under cooling with ice and then 24 hours at room temperature. The precipitate was filtered and the filtrate was concentrated under reduced pressure. To the residue was added 15 ml of methanol, and the solution was added dropwise to 400 ml of ether, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 20 ml of methanol and 2.07 ml of concentrated hydrochloric acid, and the solution was added dropwise to a mixed liquid of 200 ml of ether and 200 ml of acetone, followed by stirring for 24 hours under cooling with ice. Then, the precipitate was collected by filtration to obtain 1.42 g of the desired product.

$^1$H-NMR (DMSO-$d_6$) δ ppm:

| | |
|---|---|
| 10.82 (1H, brs) | 7.70 (1H, S) |
| 9.92 (1H, brs) | 7.64 (1H, d, J=8.9 Hz) |
| 9.66 (2H, s) | 7.49 (2H, d, J=8.6 Hz) |
| 9.45 (2H, S) | 7.04 (1H, S) |

-continued

| | |
|---|---|
| 8.64 (1H, d, J=1.7 Hz) | 3.98 (2H, S) |
| 8.18-8.60 (5H, m) | 3.74 (4H, brs) |
| 8.11 (1H, d, J=8.9 Hz) | 2.89 (4H, brs) |
| 7:96 (1H, dd, J1=8.9, J2=1.7 Hz) | |

EXAMPLE 20

Preparation of 6-amidino-1-carbamoylmethyl-2-naphthyl 4-[(2-morpholinoethyl)aminoiminomethylamino)-benzoate.trihydrochloride:

30 Milliliters of 20% hydrous pyridine was added to 1.2 g of 4-[(2-morpholinoethyl)aminoiminomethylamino] benzoic acid.dihydrochloride, 1.72 g of 6-amidino-1-carbamoylmethyl-2-naphthol.hydrochloride, 1.06 g of DCC and 52.4 mg of DMAP, followed by stirring for 2 hours under cooling with ice and then 48 hours at room temperature. The precipitate was filtered and the filtrate was concentrated under reduced pressure. To the residue was added 15 ml of DMF, and the solution was added dropwise to 400 ml of acetone, followed by stirring for 24 hours under cooling with ice. Then, the precipitate was collected by filtration to obtain a crude product. Then, the product was subjected to silica gel column chromatography using methyl ethyl ketone-water-formic acid (80:15:5) as an eluent, and the desired fractions were collected and the solvent was distilled off under reduced pressure. To the residue were added 15 ml of methanol and 2.2 ml of concentrated hydrochloric acid, and the solution was added dropwise to 450 ml of acetone, followed by stirring for 15 minutes under cooling with ice. Then, the precipitate was collected by filtration to obtain 840 mg of the desired product.

$^1$H-NMR (DMSO-$d_6$) δ ppm:

| | |
|---|---|
| 11.59 (1H, brs) | 8.10 (1H, d, J=8.9 Hz) |
| 10.77 (1H, S) | |
| 7.95 (1H, dd, J1=8.9, J2=1.7 Hz) | |
| 9.66 (2H, S) | 7.69 (1H, S) |
| 9.44 (2H, S) | 7.64 (1H, d, J=8.9 Hz) |
| 8.68 (1H, S) | 7.53 (2H, d, J=8.6 Hz) |
| 8.64 (1H, d, J=1.7 Hz) | 7.03 (1H, S) |
| 8.48 (2H, brs) | 3.73–4.14 (8H, m) |
| 8.30 (1H, d, J=8.9 Hz) | 3.00–3.65 (6H, m) |
| 8.22 (2H, d, J=8.6 Hz) | |

EXAMPLE 21

Preparation of 6-amidino-1-carbamoylmethyl-2-naphthyl 4-[(3-morpholinopropyl)aminoiminomethylamino) benzoate.trihydrochloride:

30 Milliliters of 20% hydrous pyridine was added to 1.2 g of 4-[(3-morpholinopropyl)aminoiminomethylamino] benzioc acid.dihydrochloride, 1.79 g of 6-amidino-1-carbamoylmethyl-2-naphthol.hydrochloride, 1.06 g of DCC and 52.4 mg of DMAP, followed by stirring for 2 hours under cooling with ice and then 48 hours at room temperature. The precipitate was filtered and the filtrate was concentrated under reduced pressure. To the residue was added 30 ml of DMF, and the solution was added dropwise to a mixed liquid of 300 ml of acetone and 100 ml of ether, followed by stirring for 24 hours under cooling with ice. Then, the precipitate was collected by filtration to obtain a crude product. Then, the product was subjected to silica gel column chromatography using methyl ethyl ketone-water-formic acid (80:15:5) as an eluent, and the desired fractions were collected and the solvent was distilled off under reduced pressure. To the residue were added 30 ml of methanol and 792 μl of concentrated hydrochloric acid, and the solution was added dropwise to 400 ml of acetone, followed by stirring for 24 hours under cooling with ice. Then, the precipitate was collected by filtration to obtain 1.07 g of the desired product.

$^1$H-NMR (DMSO-$d_6$) δ ppm:

| | |
|---|---|
| 11.57 (1H, brs) | |
| 7.96 (1H, dd, J1=8.9, J2=1.7 Hz) | |
| 10.70 (1H, S) | 7.70 (1H, S) |
| 9.66 (2H, S) | 7.64 (1H, d, J=8.9Hz) |
| 9.44 (2H, S) | 7.50 (2H, d, J=8.6Hz) |
| 8.64 (1H, d, J=1.7 Hz) | 7.03 (1H, S) |
| 8.60 (1H, brs) | 3.75–4.09 (6H, m) |
| 8.36 (1H, brs) | 3.34–3.57 (4H,m) |
| 8.30 (1H, d, J=8.9 Hz) | 2.92–3.29 (4H, m) |
| 8.23 (2H, d, J=8.6 Hz) | 1.92–2.18 (2H, m) |
| 8.10 (1H, d, J=8.9 Hz) | |

EXAMPLE 22

Preparation of 6-amidino-1-carbamoylmethyl-2-naphthyl 4-[(3-morpholinopropyl)iminomethylaminomethylamino) benzoate-trihydrochloride:

20 Milliliters of 20% hydrous pyridine was added to 1.13 g of 4-[(3-morpholinopropyl)iminomethylaminothylamino] benzoic acid.dihydrochloride, 800 mg of 6-amidino-1-carbamoylmethyl-2-naphthol.hydrochloride, 708 mg of DCC and 34.9 mg of DMAP, followed by stirring for 2 hours under cooling with ice and then 24 hours at room temperature. Furthermore, 354 mg of DCC was added, followed by stirring for 24 hours at room temperature. The precipitate was filtered and the filtrate was concentrated under reduced pressure. To the residue was added 30 ml of DMF, and the solution was added dropwise to a mixed liquid of 300 ml of acetone and 100 ml of ether, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 5 ml of DMF and 716 μl of concentrated hydrochloric acid, and the solution was added dropwise to a mixed liquid of 250 ml of acetone and 100 ml of ether, followed by stirring for 24 hours under cooling with ice. Then, the precipitate was collected by filtration to obtain 972.7 mg of the desired product.

$^1$H-NMR (DMSO-$d_6$) δ ppm:

| | |
|---|---|
| 11.56 (1H, brs) | 7.55 (2H, d, J=8.6 Hz) |
| 10.42 (1H, S) | 7.04 (1H, S) |
| 9.66 (2H, S) | 3.72–4.17 (6H, m) |
| 9.44 (2H, S) | 3.28–3.65 (4H, m) |
| 7.84–8.90 (8H, m) | 2.80–3.26 (7H, m) |
| 7.71 (1H, S) | 1.90–2.22 (2H, m) |
| 7.63 (1H, d, J=8.9 Hz) | |

EXAMPLE 23

Preparation of 6-amidino-1-carbamoylmethyl-2-naphthyl 4-[(4-morpholinobutyl)aminoiminomethylamino]-benzoate.trihydrochloride:

20 Milliliters of 20% hydrous pyridine was added to 1.05 g of 4-[(4-morpholinobutyl)aminoiminomethylamino] benzoic acid.dihydrochloride, 735.7 mg of 6-amidino-1- carbamoylmethyl-2-naphthol.hydrochloride, 660 mg of DCC and 32.6 mg of DMAP, followed by stirring for 2 hours under cooling with ice and then 48 hours at room temperature. The precipitate was filtered and the filtrate was concentrated under reduced pressure. To the residue was added 5 ml of DMF, and the solution was added dropwise to 400 ml of acetone, followed by stirring for 1 hour under cooling with ice. Then, the precipitate was collected by filtration to obtain a crude product. Then, the product was subjected to silica gel column chromatography using methyl ethyl ketone-water-formic acid (80:15:5) as an eluent, and the desired fractions were collected and the solvent was distilled off under reduced pressure. To the residue were added 10 ml of methanol and 1.2 ml of concentrated hydrochloric acid, and the solution was added dropwise to 400 ml of acetone, followed by stirring for 24 hours under cooling with ice. Then, the precipitate was collected by filtration to obtain 885.3 mg of the desired product.

$^1$H-NMR (DMSO-$d_6$) δ ppm:

| | |
|---|---|
| 11.52 (1H, brs) | |
| 7.96 (1H, dd, J1=8.9, J2=1.7 Hz) | |
| 10.66 (1H, S) | 7.70 (1H, S) |
| 9.66 (2H, S) | 7.64 (1H, d, J=8.9 Hz) |
| 9.45 (2H, S) | 7.48 (2H, d, J=8.6 Hz) |
| 8.65 (1H, d, J=1.7 Hz) | 7.03 (1H, S) |
| 8.61 (1H, brs) | 3.74–4.12 (6H, m) |
| 8.15–8.45 (5H, m) | 2.84–3.56 (8H, m) |
| 8.10 (1H, d, J=8.9 Hz) | 1.49–1.97 (4H, m) |

EXAMPLE 24

Preparation of 6-amidino-1-carbamoylmethyl-2-naphthyl 4-[2-(1-pyrrolidinyl)ethyl]aminoiminomethylamino]benzoate.trihydrochloride:

30 Milliliters of 20% hydrous pyridine was added to 1.51 g of 4-[2-(1-pyrrolidinyl)ethyl]aminoiminomethylamino] benzoic acid.dihydrochloride, 1.1 g of 6-amidino-1-carbamoylmethyl-2-naphthol.hydrochloride, 973 mg of DCC and 48 mg of DMAP, followed by stirring for 2 hours under cooling with ice and then 24 hours at room temperature. The precipitate was filtered and the filtrate was concentrated under reduced pressure. To the residue was added 15 ml of DMF, and the solution was added dropwise to 300 ml of acetone, followed by stirring for 24 hours under cooling with ice. Then, the precipitate was collected by filtration to obtain a crude product. Then, the product was subjected to silica gel column chromatography using methyl ethyl ketone-water-formic acid (80:15:5) as an eluent, and the desired fractions were collected and the solvent was distilled off under reduced pressure. To the residue were added 20 ml of methanol and 3.7 ml of concentrated hydrochloric acid, and the solution was added dropwise to 200 ml of acetone, followed by stirring for 2 hours under cooling with ice. Then, the precipitate was collected by filtration, and to the collected precipitate were added 5 ml of ethanol and then 10 ml of methanol, followed by stirring for 1 hour under cooling with ice. The precipitate was collected by filtration and washed with a small amount of acetone to obtain 1.21 g of the desired product.

$^1$H-NMR (DMSO-$d_6$) δ ppm:

| | |
|---|---|
| 11.18(1H, brs) | 8.10(1H, d, J=8.9Hz) |
| 10.75(1H, S) | 7.97(1H, d, J=8.9Hz) |
| 9.67(2H, S) | 7.70(1H, S) |
| 9.45(2H, S) | 7.64(1H, d, J=8.9Hz) |
| 8.69(2H, S) | 7.53(2H, d, J=8.6Hz) |
| 8.65(1H, S) | 7.04(1H, S) |
| 8.48(1H, brs) | 3.98(2H, S) |
| 8.30(1H, d, J=8.9Hz) | 2.92–3.91(8H, m) |
| 8.22(2H, d, J=8.6Hz) | 1.73–2.14(4H, m) |

EXAMPLE 25

Preparation of 6-amidino-1-carbamoylmethyl-2-naphthyl 4-[(2-piperidinoethyl)aminoiminomethylamino]-benzoate.trihydrochloride:

30 Milliliters of 20% hydrous pyridine was added to 1.71 g of 4-[(2-piperidinoethyl)aminoiminomethylamino] benzoic acid.dihydrochloride, 1.2 g of 6-amidino-1-carbamoylmethyl-2-naphthol.hydrochloride, 1.06 g of DCC and 52.4 mg of DMAP, followed by stirring for 2 hours under cooling with ice and then 4 days at room temperature. The precipitate was filtered and the filtrate was concentrated under reduced pressure. To the residue was added 15 ml of DMF, and the solution was added dropwise to a mixed liquid of 300 ml of acetone and 100 ml of ether, followed by stirring for 24 hours under cooling with ice. Then, the precipitate was collected by filtration to obtain a crude product. Then, the product was subjected to silica gel column chromatography using methyl ethyl ketone-water-formic acid (80:15:5) as an eluent, and the desired fractions were collected and the solvent was distilled off under reduced pressure. To the residue were added 20 ml of methanol and 2.1 ml of concentrated hydrochloric acid, and the solution was added dropwise to 450 ml of acetone, followed by stirring for 30 minutes under cooling with ice. Then, the precipitate was collected by filtration to obtain 1.08 g of the desired product.

$^1$H-NMR (DMSO-$d_6$) δ ppm:

| | |
|---|---|
| 10.86(1H, brs) | 8.10(1H, d, J=8.9Hz) |
| 10.79(1H, S) | |
| 7.97(1H, dd, J1=8.9, J2=1.7Hz) | |
| 9.67(2H, S) | 7.70(1H, S) |
| 9.46(2H, S) | 7.64(1H, d, J=8.9Hz) |
| 8.71(1H, brs) | 7.52(2H, d, J=8.6Hz) |
| 8.65(1H, d, J=1.7Hz) | 7.04(1H, S) |
| 8.48(2H, brs) | 3.72–4.10(4H, m) |
| 8.30(1H, d, J=8.9Hz) | 2.70–3.60(8H, m) |
| 8.22(2H, d, J=8.6Hz) | 1.57–2.01(4H, m) |

EXAMPLE 26

Preparation of 6-amidino-1-carbamoylmethyl-2-naphthyl 4-methylaminoiminomethylaminobenzoate.dihydrochloride:

20 Milliliters of 20% hydrous pyridine was added to 600 mg of 4-methylaminoiminomethylaminobenzoic acid.hydrochloride, 730 mg of 6-amidino-1-carbamoylmethyl-2-naphthol.hydrochloride, 646 mg of DCC and 32 mg of DMAP, followed by stirring for 2 hours under cooling with ice and then 48 hours at room temperature. The precipitate was filtered and the filtrate was concentrated under reduced pressure. To the residue was added 20 ml of DMF, and the solution was added dropwise to 300 ml of acetone, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 15 ml of methanol and 440 μl of concentrated hydrochloric acid, and the solution was added dropwise to a mixed liquid of 300 ml of acetone and 100 ml of ether, followed by stirring for 24 hours under cooling with ice. Then, the precipitate was collected by filtration to obtain 661.1 mg of the desired product.

$^1$H-NMR (DMSO-d$_6$) δ ppm:

| | |
|---|---|
| 10.64(1H, brs) | 7.63(1H, d, J=8.9Hz) |
| 9.67(2H, S) | 7.47(2H, d, J=8.6Hz) |
| 9.46(2H, S) | 7.03(1H, S) |
| 8.64(1H, d, J=1.7Hz) | 3.98(2H, S) |
| 7.86–8.54(8H, m) | 2.91(3H, d, J=4.6Hz) |
| 7.69(1H, S) | |

EXAMPLE 27

Preparation of 6-amidino-1-carbamoylmethyl-2-naphthyl 4-methylaminomethyliminomethylaminobenzoate.dihydrochloride:

80 Milliliters of 20% hydrous pyridine was added to 5.76 g of 4-methylaminomethyliminomethylaminobenzoic acid.hydrochloride, 6.0 g of 6-amidino-1-carbamoylmethyl-2-naphthol.hydrochloride, 5.3 g of DCC and 217 mg of DMAP, followed by stirring for 2 hours under cooling with ice and then 5 days at room temperature. Then, the precipitate was collected by filtration and washed with 120 ml of warm DMF. To this collected precipitate was added 300 ml of water, followed by stirring for 24 hours at room temperature, and the precipitate was filtered. Each of the reaction filtrate, warm DMF wash liquid and aqueous filtrate obtained above was concentrated under reduced pressure. The resulting residues were combined and 70 ml of DMF was added thereto. The solution was added dropwise to 700 ml of acetone, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 50 ml of methanol and 3.3 ml of concentrated hydrochloric acid, and the solution was added dropwise to a mixed liquid of 500 ml of acetone and 200 ml of ether, followed by stirring for 24 hours under cooling with ice. Then, the precipitate was collected by filtration to obtain 5.78 g of the desired product.

$^1$H-NMR (DMSO-d$_6$) δ ppm:

| | |
|---|---|
| 10.31(1H, S) | |
| 7.97(1H, dd, J1=8.9, J2=1.7Hz) | |
| 9.69(2H, S) | 7.73(1H, S) |
| 9.48(2H, S) | 7.63(1H, d, J=8.9Hz) |
| 8.66(1H, d, J=1.7Hz) | 7.51(2H, d, J=8.6Hz) |
| 8.40(2H, brs) | 7.05(1H, S) |
| 8.30(1H, d, J=8.9Hz) | 3.98(2H, S) |
| 8.21(2H, d, J=8.6Hz) | 2.94(6H, S) |
| 8.10(1H, d, J=8.9Hz) | |

EXAMPLE 28

Preparation of 6-amidino-1-carbamoylmethyl-2-naphthyl 4-n-butylaminoiminomethylaminobenzoate.dihydrochloride:

30 Milliliters of 20% hydrous pyridine was added to 1.6 g of 4-n-butylaminoiminomethylaminobenzoic acid.hydrochloride, 1.5 g of 6-amidino-1-carbamoylmethyl-2-naphthol.hydrochloride, 1.33 g of DCC and 65.5 mg of DMAP, followed by stirring for 2 hours under cooling with ice and then 4 days at room temperature. Then, the precipitate was filtered and the filtrate was concentrated under reduced pressure. To the residue was added 20 ml of DMF, and the solution was added dropwise to a mixed liquid of 300 ml of acetone and 200 ml of ether, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 30 ml of methanol and 2.1 ml of concentrated hydrochloric acid, and the solution was added dropwise to 250 ml of acetone, followed by stirring for 24 hours under cooling with ice. Then, the precipitate was collected by filtration, and to the collected precipitate were added 9 ml of methanol, 7 ml of ethanol and 6 ml of 2-propanol, followed by stirring for 1 hour under cooling with ice. The precipitate was collected by filtration and washed with a small amount of acetone to obtain 1.68 g of the desired product.

$^1$H-NMR (DMSO-d$_6$) δ ppm:

| | |
|---|---|
| 10.59(1H, S) | 7.63(1H, d, J=8.9Hz) |
| 9.66(2H, S) | 7.46(2H, d, J=8.6Hz) |
| 9.44(2H, S) | 7.03(1H, S) |
| 8.64(1H, d, J=1.7Hz) | 3.98(2H, S) |
| 8.53(1H, brs) | 3.20–3.45(2H, m) |
| 7.85–8.45(7H, m) | 1.24–1.67(4H, m) |
| 7.68(1H, S) | 0.92(3H, t, J=7.3Hz) |

EXAMPLE 29

Preparation of 6-amidino-1-carbamoylmethyl-2-naphthyl 4-dimethylaminoiminomethylaminobenzoate.dihydrochloride:

40 Milliliters of 20% hydrous pyridine was added to 1.44 g of 4-dimethylaminoiminomethylaminobenzoic acid.hydrochloride, 1.5 g of 6-amidino-1-carbamoylmethyl-2-naphthol.hydrochloride, 1.33 g of DCC and 65.5 mg of DMAP, followed by stirring for 2 hours under cooling with ice and then 72 hours at room temperature. Then, the precipitate was filtered and the filtrate was concentrated under reduced pressure. To the residue was added 25 ml of DMF, and the resulting solution was added dropwise to a mixed liquid of 200 ml of ether and 100 ml of acetone, followed by stirring for 2 hours under cooling with ice. Then, the precipitate was collected by filtration to obtain a crude product. Then, the product was subjected to silica gel column chromatography using methyl ethyl ketone-water-formic acid (80:15:5) as an eluent, and the desired fractions were collected and the solvent was distilled off under reduced pressure. To the residue were added 15 ml of methanol and 2.8 ml of concentrated hydrochloric acid, and the resultant solution was added dropwise to 150 ml of acetone, followed by stirring for 2 hours under cooling with ice. Then, the precipitate was collected by filtration, and to the collected precipitate were added 10 ml of methanol and 5 ml of ethanol, followed by stirring for 2 hours under cooling with ice. The precipitate was collected by filtration and washed with a small amount of acetone to obtain 966 mg of the desired product.

$^1$H-NMR (DMSO-d$_6$) δ ppm:

| | |
|---|---|
| 10.43(1H, S) | |
| 7.97(1H, dd, J1=8.9, J2=1.7Hz) | |
| 9.69(2H, S) | 7.71(1H, S) |
| 9.48(2H, S) | 7.63(1H, d, J=8.9Hz) |
| 8.66(1H, d, J=1.7Hz) | 7.48(2H, d, J=8.6Hz) |
| 8.25–8.40(3H, m) | 7.04(1H, S) |
| 8.21(2H, d, J=8.9Hz) | 3.98(2H, S) |
| 8.10(1H, d, J=8.9Hz) | 3.14(6H, S) |

EXAMPLE 30

Preparation of 6-amidino-1-carbamoylmethyl-2-naphthyl 4-aminoiminomethylbenzoate.dihydrochloride:

20 Milliliters of 20% hydrous pyridine and 6 ml of DMF were added to 1.0 g of 4-aminoiminomethylbenzoic acid.hydrochloride, 1.39 g of 6-amidino-1-carbamoylmethyl-2-naphthol.hydrochloride, 1.23 g of DCC and 60.8 mg of DMAP, followed by stirring for 2 hours under cooling with ice and then 24 hours at room temperature. Then, the precipitate was filtered and the filtrate was concentrated under reduced pressure. To the residue was added 20 ml of DMF, and the resulting solution was added dropwise to 400 ml of acetone, followed by stirring for 24 hours under cooling with ice. Then, the precipitate was collected by filtration to obtain a crude product. Then, the product was subjected to silica gel column chromatography using methyl ethyl ketone-water-formic acid (80:15:5) as an eluent, and the desired fractions were collected and the solvent was distilled off under reduced pressure. To the residue were added 10 ml of methanol and 0.9 ml of concentrated hydrochloric acid, and the resulting solution was added dropwise to 200 ml of acetone, followed by stirring for 2 hours under cooling with ice. Then, the precipitate was collected by filtration to obtain 80.2 mg of the desired product.

$^1$H-NMR (DMSO-d$_6$) δ ppm:

| | |
|---|---|
| 9.70(2H, S) | 8.03–8.18(3H, m) |
| 9.61(2H, S) | 7.909–8.00(1H, m) |
| 9.48(2H, S) | 7.70(1H, d, J=8.9Hz) |
| 9.36(2H, S) | 7.65(1H, S) |
| 8.62(1H, S) | 7.00(1H, S) |
| 8.28–8.46(3H, m) | 4.01(2H, S) |

EXAMPLE 31

Preparation of 6-amidino-1-carbamoylmethyl-2-naphthyl 4-[(4,5-dihydrothiazol-2-yl)amino]-benzoate.dihydrochloride:

15 Milliliters of 20% hydrous pyridine was added to 1.5 g of 4-[(4,5-dihydrothiazol-2-yl)amino]benzoic acid.hydrochloride, 1.62 g of 6-amidino-1-carbamoylmethyl-2-naphthol.hydrochloride, 1.43 g of DCC and 70.8 mg of DMAP, followed by stirring for 2 hours under cooling with ice and then 24 hours at room temperature. Then, the precipitate was filtered and the filtrate was concentrated under reduced pressure. To the residue was added 20 ml of DMF, and the resulting solution was added dropwise to a mixed liquid of 200 ml of acetone and 200 ml of ether, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 10 ml of methanol and 0.97 ml of concentrated hydrochloric acid, and the solution was added dropwise to a mixed liquid of 150 ml of acetone and 50 ml of ether, followed by stirring for 24 hours under cooling with ice. Then, the precipitate was collected by filtration to obtain 651 mg of the desired product.

$^1$H-NMR (DMSO-d$_6$) δ ppm:

| | |
|---|---|
| 9.66(2H, S) | |
| 7.94(1H, dd, J1=8.9, J2=1.7Hz) | |
| 9.45(2H, S) | 7.52–7.79(4H, m) |
| 8.64(1H, d, J=1.7Hz) | 7.04(1H, S) |
| 8.32(1H, d, J=8.9Hz) | 3.87–4.18(4H, m) |
| 8.22(2H, d, J=8.6Hz) | 3.45–3.67(2H, m) |
| 8.09(1H, d, J=8.9Hz) | |

Reference Example 8

Preparation of 6-cyano-1-carboxy-2-naphthol:

A solution prepared by dissolving 71 g of potassium hydroxide in 1.5 liter of water was added to a solution prepared by dissolving 24.0 g of 6-cyano-1-methoxycarbonyl-2-naphthol in 4.7 liters of methanol, followed by stirring at 50°–60° C. for 24 hours. After cooling, the reaction mixture was made to an acidic solution with addition of 10% hydrochloric acid. The precipitate was collected by filtration and washed with a small amount of water to obtain 14.8 g of the desired product.

$^1$H-NMR (DMSO-d$_6$) δ ppm:

| | |
|---|---|
| 8.49(1H, d, J=1.7Hz) | 8.44(1H, d, J=8.9Hz) |
| 8.12(1H, d, J=8.9Hz) | |
| 7.82(1H, dd, J1=8.9, J2=1.7Hz) | |
| 7.36(1H, d, J=8.9Hz) | |

EXAMPLE 32

Preparation of 6-amidino-1-carboxy-2-naphthol.methanesulfonate:

To 1.0 g of 6-cyano-1-carboxy-2-naphthol was added 100 ml of anhydrous methanol, and dry hydrogen chloride gas was passed through the solution under cooling with ice and stirring to saturate the solution with hydrogen chloride gas. Thereafter, the resulting solution was further stirred for 72 hours under cooling with water. The solution was added dropwise to 600 ml of anhydrous ether, followed by stirring for 1 hour under cooling with ice. The resulting precipitate was collected by filtration, and 50 ml of anhydrous methanol was added to the collected precipitate, and dry ammonia gas was passed through the solution under cooling with ice and stirring to saturate with ammonia gas and the resulting solution was further stirred for 72 hours under cooling with water. The precipitate was collected by filtration and washed with a mixed liquid of 20 ml of water and 20 ml of acetone. To this collected precipitate were added 10 ml of DMF and 0.8 ml of methanesulfonic acid, and the solution was added dropwise to 400 ml of ether, followed by stirring for 1 hour under cooling with ice. The precipitate was collected by filtration and washed with a small amount of acetone to obtain 1.19 g of the desired product.

¹H-NMR (DMSO-d₆) δ ppm:

| | |
|---|---|
| 9.39(2H, S) | |
| 7.89(1H, dd, J1=9.2, J2=2.0Hz) | |
| 9.14(2H, S) | 7.37(1H, d, J=8.9Hz) |
| 8.39–8.62(2H, m) | 2.44(3H, S) |
| 8.15(1H, d, J=8.9Hz) | |

EXAMPLE 33

Preparation of 6-amidino-1-carboxy-2-naphthyl 4-[(4,5-dihydro-1H-imidzol-2-yl)amino]benzoate.dimethanesulfonate:

To 1.25 g of 6-amidino-1-carboxy-2-naphthol.methanesulfonate was added 20 ml of anhydrous pyridine, and then thereto was added 1.0 g of 4-[(4,5-dihydro-1H-imidzol-2-yl)amino]benzoic acid chloride.hydrochloride, followed by stirring for 2 hours under cooling with ice and 24 hours under cooling with water in a nitrogen gas stream. The precipitate was filtered and the filtrate was concentrated under reduced pressure. To the residue were added 60 ml of DMF and then 1 ml of methanesulfonic acid. The precipitate was filtered and the filtrate was concentrated under reduced pressure. To the residue was added 15 ml of DMF, and the solution was added dropwise to a mixed liquid of 100 ml of acetone and 100 ml of ether, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 10 ml of DMF and 0.5 ml of methanesulfonic acid. The resulting solution was added dropwise to 400 ml of acetone, followed by stirring for 24 hours under cooling with ice. Then, the precipitate was collected by filtration to obtain 715 mg of the desired product.

¹H-NMR (DMSO-d₆) δ ppm:

| | |
|---|---|
| 11.26(1H, S) | 8.19(2H, d, J=8.6Hz) |
| 9.60(2H, S) | |
| 8.00(1H, dd, J1=8.9, J2=1.7Hz) | |
| 9.38(2H, S) | 7.76(1H, d, J=8.9Hz) |
| 8.79(2H, S) | 7.51(2H, d, J=8.6Hz) |
| 8.68(1H, d, J=1.7Hz) | 3.75(4H, S) |
| 8.35(1H, d, J=8.9Hz) | 2.41(6H, S) |
| 8.24(1H, d, J=8.9Hz) | |

EXAMPLE 34

Preparation of 6-amidino-1-carboxy-2-naphthyl 4-aminoiminomethylaminobenzoate.dimethanesulfonate:

To 930 mg of 6-amidino-1-carboxy-2-naphthol.methanesulfonate were added 10 ml of anhydrous pyridine and then 667.5 mg of 4-aminoiminomethylaminobenzoic acid chloride.hydrochloride, followed by stirring for 2 hours under cooling with ice and then 48 hours under cooling with water. The precipitate was collected by filtration and washed with a small amount of pyridine. To the collected precipitated were added 20 ml of warm DMF and then 0.6 ml of methanesulfonic acid. The resulting solution was added dropwise to 600 ml of ether, followed by stirring for 1 hour under cooling with ice. The supernatant liquid was decanted, and 20 ml of methanol was added to the residue. This solution was added dropwise to 450 ml of acetone, followed by stirring for 15 minutes under cooling with ice. Then, the precipitate was collected by filtration and washed with a small amount of acetone to obtain 869 mg of the desired product.

¹H-NMR (DMSO-d₆) δ ppm:

| | |
|---|---|
| 10.27(1H, S) | 8.18(2H, d, J=8.6Hz) |
| 9.54(2H, S) | |
| 7.98(1H, dd, J1=8.9, J2=1.7Hz) | |
| 9.27(2H, S) | 7.89(4H, S) |
| 8.65(1H, d, J=1.7Hz) | 7.75(1H, d, J=8.9Hz) |
| 8.36(1H, d, J=9.2Hz) | 7.47(2H, d, J=8.6Hz) |
| 8.25(1H, d, J=9.2Hz) | 2.44(6H, S) |

EXAMPLE 35

Preparation of 6-amidino-1-methoxycarbonyl-2-naphthyl 4-[(4,5-dihydro-1H-imidazol-2-yl)amino]-benzoate.dihydrochloride:

30 Milliliters of 20% hydrous pyridine was added to 1.06 g of 4-[(4,5-dihydro-1H-imidazol-2-yl)amino]benzoic acid.methanesulfonate, 1.2 g of 6-amidino-1-methoxycarbonyl-2-naphthol.methanesulfonate, 872 mg of DCC and 43 mg of DMAP, followed by stirring for 2 hours under cooling with ice and 24 hours at room temperature. Furthermore, 436 mg of DCC and 7 ml of DMF were added, followed by stirring for 72 hours at room temperature. The precipitate was filtered and the filtrate was concentrated under reduced pressure. To the residue was added 15 ml of DMF. The resulting solution was added dropwise to 200 ml of acetone, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 15 ml of methanol and 2.4 ml of concentrated hydrochloric acid. The resulting solution was added dropwise to a mixed liquid of 100 ml of acetone and 200 ml of ether, followed by stirring for 1 hour under cooling with ice. Then, the precipitate was collected by filtration to obtain 600.6 mg of the desired product.

¹H-NMR (DMSO-d₆) δ ppm:

| | |
|---|---|
| 11.71(1H, S) | 8.13–8.31(3H, m) |
| 9.76(2H, S) | |
| 8.04(1H, dd, J1=8.9, J2=1.7Hz) | |
| 9.54(2H, S) | 7.78(1H, d, J=8.9Hz) |
| 8.80(2H, S) | 7.54(2H, d, J=8.6Hz) |
| 8.75(1H, d, J=1.7Hz) | 3.86(3H, S) |
| 8.39(1H, d, J=8.9Hz) | 3.74(4H, S) |

EXAMPLE 36

Preparation of 6-amidino-1-methoxycarbonyl-2-naphthyl 4-aminoiminomethylaminobenzoate.dimethanesulfonate:

50 Milliliters of anhydrous pyridine was added to 1.9 g of 4-aminoiminomethylaminobenzoic acid.hydro-chloride, 3.0 g of of 6-amidino-1-methoxycarbonyl-2-naphthol.methanesulfonate, and 2.2 g of DCC, followed by stirring for 2 hours under cooling with ice and 24 hours at room temperature. The precipitate was collected by filtration and washed with a small amount of pyridine. To the collected precipitate was added 30 ml of water, followed by stirring for 1 hour. Insoluble matter was filtered off and the filtrate was added dropwise to 100 ml of saturated aqueous sodium bicarbonate solution, followed by stirring for 24 hours under cooling with ice. Then, the precipitate was collected by filtration and washed with a small amount of water and acetone. To the collected precipitate were added 15 ml of methanol and 2.2 ml of methanesulfonic acid. The resulting solution was added dropwise to 300 ml of ether, followed by stirring for 24 hours under cooling with ice. Then, the precipitate was collected by filtration and washed with a small amount of acetone to obtain 2.46 g of the desired product.

$^1$H-NMR (DMSO-$d_6$) δ ppm:

| | |
|---|---|
| 10.28(1H, S) | |
| 7.98(1H, dd, J1=8.9, J2=1.7Hz) | |
| 9.55(2H, S) | 7.90(4H, S) |
| 9.29(2H, S) | 7.78(1H, d, J=8.9Hz) |
| 8.67(1H, d, J=1.7Hz) | 7.47(2H, d, J=8.6Hz) |
| 8.41(1H, d, J=9.2Hz) | 3.87(3H, S) |
| 8.22(1H, d, J=9.2Hz) | 2.42(6H, S) |
| 8.17(2H, d, J=8.6Hz) | |

EXAMPLE 37

Preparation of 6-amidino-1-carboxymethyl-2-naphthol.methanesulfonate:

To 12.4 g of 6-amidino-1-carbamoylmethyl-2-naphthol was added 370 g of 25% hydrochloric acid, followed by stirring at 70° C. for 2.5 hours. After cooling with water, the precipitate was collected by filtration and washed with 80 g of 15% hydrochloric acid. The collected precipitate was added to a solution prepared by adding 200 ml of water to 10 g of sodium bicarbonate, followed by stirring for 1 hour at room temperature, and the resulting precipitate was collected by filtration and washed with water. This collected precipitate was added to a solution of 13 ml of methanesulfonic acid in 180 ml of water to dissolve the precipitate at 50° C. Furthermore, 1.0 g of active carbon was added to the solution, followed by stirring for 1 hour at room temperature. Thereafter, insoluble matter was filtered off and the filtrate was concentrated to 90 ml under reduced pressure. This solution was stirred for 24 hours under cooling with water. Then, the precipitate was collected by filtration and washed with a small amount of acetone and ether to obtain 12.3 g of the desired product.

$^1$H-NMR (DMSO-$d_6$) δ ppm:

| | |
|---|---|
| 12.27(1H, br) | 7.90(1H, d, J=8.9Hz) |
| 10.41(1H, S) | |
| 7.77(1H, dd, J=8.9, J2=1.7Hz) | |
| 9.33(2H, S) | 7.36(1H, d, J=8.9Hz) |
| 9.04(2H, S) | 4.00(2H, S) |
| 8.41(1H, d, J=1.7Hz) | 2.42(3H, S) |
| 7.99(1H, d, J=8.9Hz) | |

EXAMPLE 38

Preparation of 6-amidino-1-methoxycarbonyl-methyl-2-naphthol.methanesulfonate:

To 6.0 g of 6-amidino-1-carboxymethyl-2-naphthol.methanesulfonate was added 200 ml of anhydrous methanol, and dry hydrogen chloride gas was passed therethrough to saturate the solution with hydrogen chloride gas under cooling with ice and stirring. Thereafter, the resulting solution was further stirred for 24 hours under cooling with water. The reaction mixture was concentrated under reduced pressure, and to the residue was added 300 ml of ether, followed by stirring for 24 hours under cooling with ice. The resulting precipitate was collected by filtration, and 100 ml of 0.5% dry ammonia gas-containing methanol was added to the collected precipitate, followed by stirring for 1 hour under cooling with ice. The precipitate was collected by filtration and washed with a small amount of water and acetone. To the collected precipitate were added 100 ml of methanol and 2.02 ml of methanesulfonic acid, followed by stirring for 2 hours under cooling with ice. The solution was concentrated under reduced pressure, and to the residue was added 200 ml of acetone, followed by stirring for 1 hour under cooling with ice. The resulting precipitate was collected by filtration to obtain 5.0 g of the desired product.

$^1$H-NMR (DMSO-$d_6$) δ ppm:

| | |
|---|---|
| 10.49(1H, S) | |
| 7.78(1H, dd, J1=8.9, J2=1.7Hz) | |
| 9.33(2H, S) | 7.37(1H, d, J=8.9Hz) |
| 9.05(2H, S) | 4.10(2H, S) |
| 8.41(1H, d, J=1.7Hz) | 3.60(3H, S) |
| 8.00(1H, d, J=8.9Hz) | 2.42(3H, S) |
| 7.92(1H, d, J=8.9Hz) | |

EXAMPLE 39

Preparation of 6-amidino-1-methoxycarbonylmethyl-2-naphthyl 4-[(4,5-dihydro-1H-imidazol-2-yl)amino]benzoate.dimethanesulfonate:

60 Milliliters of 20% hydrous pyridine was added to 2.8 g of 4-[(4,5-dihydro-1H-imidazol-2-yl)amino]benzoic acid.methanesulfonate, 3.0 g of 6-amidino-1-methoxycarbonylmethyl-2-naphthol.methanesulfonate, 4.19 g of DCC and 103.4 mg of DMAP, followed by stirring for 2 hours under cooling with ice and 48 hours at room temperature. The precipitate was filtered and the filtrate was concentrated under reduced pressure. To the residue was added 15 ml of DMF. The solution was added dropwise to a mixed liquid of 500 ml of acetone and 300 ml of ether, followed by stirring for 24 hours under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 40 ml of methanol and 0.83 ml of methanesulfonic acid. The resulting solution was added dropwise to 400 ml of acetone, followed by stirring for 30 minutes under cooling with ice. Then, the precipitate was collected by filtration to obtain 1.4 g of the desired product.

$^1$H-NMR (DMSO-$d_6$) δ ppm:

| | |
|---|---|
| 11.02(1H, S) | |
| 7.94(1H, dd, J1=8.9, J2=1.7Hz) | |
| 9.51(2H, S) | 7.69(1H, d, J=8.9Hz) |
| 9.26(2H, S) | 7.50(2H, d, J=8.9Hz) |
| 8.76(2H, S) | 4.24(2H, S) |
| 8.61(1H, d, J=1.7Hz) | 3.76(4H, S) |
| 8.37(1H, d, J=8.9Hz) | 3.53(3H, S) |
| 8.23(2H, d, J=8.9Hz) | 2.41(6H, S) |
| 8.19(1H, d, J=8.9Hz) | |

EXAMPLE 40

Preparation of 6-amidino-1-carboxymethyl-2-naphthyl 4-[(4,5-dihydro-1H-imidazol-2-yl)amino]-benzoate.dimethanesulfonate:

45 Milliliters of 10% aqueous methanesulfonic acid solution was added to 500 mg of 6-amidino-1-methoxycarbonylmethyl-2-naphthyl 4-[(4,5-dihydro-1H-imidazol-2-yl)amino]benzoate.dimethanesulfonate, followed by stirring for 5 hours at 80° C. After leaving the mixture for cooling, 350 mg of active carbon was added to the reaction mixture, followed by stirring for 30 minutes at room temperature. Insoluble matter was filtered off and the filtrate was concentrated under reduced pressure. To the residue was added a small amount of water. The solution was added dropwise to a mixed liquid of 150 ml of acetone and 50 ml of ether, followed by stirring for 1 hour under cooling with ice. Then, the precipitate was collected by filtration and washed with a small amount of acetone to obtain 236.1 mg of the desired product.

$^1$H-NMR (DMSO-$d_6$) δ ppm:

| | |
|---|---|
| 11.02(1H, brs) | 8.16(1H, d, J=8.9Hz) |
| 9.50(2H, S) | |
| 7.94(1H, dd, J1=8.9, J2=1.7Hz) | |
| 9.25(2H, S) | 7.68(1H, d, J=8.9Hz) |
| 8.77(2H, S) | 7.50(2H, d, J=8.9Hz) |
| 8.60(1H, d, J=1.7Hz) | 4.12(2H, S) |
| 8.35(1H, d, J=8.9Hz) | 3.75(4H, S) |
| 8.24(2H, d, J=8.9Hz) | 2.43(6H, S) |

EXAMPLE 41

Preparation of 6-amidino-1-methoxycarbonylmethyl-2-naphthyl 4-aminoiminomethylaminobenzoate.dimethanesulfonate:

170 Milliliters of anhydrous pyridine and 72 ml of DMF were added to 8.1 g of 4-aminoiminomethylaminobenzoic acid.methanesulfonate, 10.0 g of 6-amidino-1-methoxycarbonylmethyl-2-naphthol.methanesulfonate, 71.6 g of DCC and 170 mg of DMAP, followed by stirring for 2 hours under cooling with ice and 24 hours at room temperature. The precipitate was filtered and washed with a small amount of DMF. The filtrate and the wash liquid were combined and this was concentrated under reduced pressure. To the residue was added 50 ml of DMF, and the resulting solution was added dropwise to 700 ml of ether, followed by stirring for 24 hours under cooling with ice. The supernatant was decanted, and then to the residue was added 200 ml of acetone, followed by stirring for 1 hour under cooling with ice. The precipitate was collected by filtration to obtain a crude product. To the collected precipitate was added 300 ml of methanol to dissolve the precipitate. To the solution was added 2 g of active carbon, followed by stirring for 30 minutes at room temperature. Insoluble matter was filtered off and the filtrate was concentrated under reduced pressure. To the residue was added 100 ml of methanol to dissolve the residue with heating. The resulting solution was added dropwise to 300 ml of acetone, followed by stirring for 24 hours under cooling with ice. Then, the precipitate was collected by filtration to obtain 4.2 g of the desired product.

$^1$H-NMR (DMSO-$d_6$) δ ppm:

| | |
|---|---|
| 10.27(1H, S) | 7.89(4H, S) |
| 9.51(2H, S) | 7.68(1H, d, J=8.9Hz) |
| 9.23(2H, S) | 7.48(2H, d, J=8.6Hz) |
| 8.61(1H, d, J=1.7Hz) | 4.23(2H, S) |
| 8.36(1H, d, J=8.9Hz) | 3.53(3H, S) |
| 8.13–8.29(3H, m) | 2.44(6H, S) |
| 7.94(1H, dd, J1=8.9, J2=1.7Hz) | |

EXAMPLE 42

Preparation of 6-amidino-1-carboxymethyl-2-naphthyl 4-aminoiminomethylaminobenzoate.dimethanesulfonate:

30 Milliliters of 20% aqueous methanesulfonic acid solution was added to 2.5 g of 6-amidino-1-methoxycarbonylmethyl-2-naphthyl 4-aminoiminomethylaminobenzoate.dimethanesulfonate, followed by stirring for 3 hours at 60° C. Then, 700 mg of active carbon was added to the reaction mixture, followed by stirring for 30 minutes at room temperature. Insoluble matter was filtered off and the filtrate was concentrated under reduced pressure. To the residue was added 30 ml of water to dissolve the residue. The solution was added dropwise to 150 ml of acetone, followed by stirring for 1 hour under cooling with ice. Then, the precipitate was collected by filtration and washed with a small amount of acetone to obtain 580 mg of the desired product.

$^1$H-NMR (DMSO-$d_6$) δ ppm:

| | |
|---|---|
| 12.53(1H, brs) | 8.16(1H, d, J=8.9Hz) |
| 10.26(1H, S) | |
| 7.92(1H, dd, J1=8.9, J2=1.7Hz) | |
| 9.50(2H, S) | 7.89(4H, S) |
| 9.22(2H, S) | 7.67(1H, d, J=8.9Hz) |
| 8.59(1H, d, J=1.7Hz) | 7.47(2H, d, J=8.6Hz) |
| 8.34(1H, d, J=8.9Hz) | 4.12(2H, S) |
| 8.23(2H, d, J=8.6Hz) | 2.44(6H, S) |

EXAMPLE 43

Preparation of 6-amidino-1-(2-carbamoylethyl)-2-naphthyl 4-aminoiminomethylaminobenzoate.methanesulfonate:

100 Milliliters of 20% hydrous pyridine was added to 3.16 g of 4-aminoiminomethylaminobenzoic acid.methanesulfonate, 2.94 g of 6-amidino-1-(2-carbamoylethyl)-2-naphthol and 4.54 g of DCC, followed by stirring for 2 hours under cooling with ice and 24 hours at room temperature. The precipitate was filtered and the filtrate was concentrated under reduced pressure. To the residue was added 20 ml of DMF. The resulting solution was added dropwise to 500 ml of acetone, followed by stirring for 24 hours under cooling with ice. Then, the precipitate was collected by filtration to obtain a crude product. To the collected precipitate was added 150 ml of methanol to dissolve the precipitate. To the solution was added 3 g of active carbon, followed by stirring for 30 minutes at room temperature. Insoluble matter was filtered off and the filtrate was concentrated under reduced pressure. To the residue was added 30 ml of methanol to dissolve the residue with heating. The resulting solution was added dropwise to 400 ml of acetone, followed by stirring for 24 hours under cooling with ice. Then, the precipitate was collected by filtration to obtain 2.5 g of the desired product.

$^1$H-NMR (DMSO-$d_6$) δ ppm:

| | |
|---|---|
| 9.20–9.90(4H, br) | 7.48(2H, d, J=8.6Hz) |
| 8.62(1H, d, J=2.0Hz) | 7.41(1H, S) |
| 8.37(1H, d, J=8.9Hz) | 6.84(1H, S) |
| 8.28(2H, d, J=8.6Hz) | 3.12–3.37(2H, m) |
| 7.72–8.17(6H, m) | 2.28–2.47(5H, m) |
| 7.61(1H, d, J=8.9Hz) | |

EXAMPLE 44

Preparation of 6-amidino-1-(2-carboxyethyl)-2-naphthyl 4-aminoiminomethylaminobenzoate.dihydrochloride:

300 Milliliters of 3.6% hydrochloric acid was added to 3.3 g of 6-amidino-1-(2-carbamoylethyl)-2-naphthyl 4-aminoiminomethylaminobenzoate.methanesulfonic acid hydrochloride, followed by stirring for 6 hours at 75°–80° C. Furthermore, the reaction mixture was stirried for 24 hours under cooling with ice. Then, the precipitate was collected by filtration and washed with a small amount of 15% hydrochloric acid and acetone to obtain 1.58 g of the desired product.

$^1$H-NMR (DMSO-d$_6$) δ ppm:

| | |
|---|---|
| 12.30(1H, brs) | 8.27(2H, d, J=8.6Hz) |
| 10.78(1H, brs) | 7.81–8.17(6H, m) |
| 9.66(2H, S) | 7.62(1H, d, J=8.9Hz) |
| 9.43(2H, S) | 7.49(2H, d, J=8.6Hz) |
| 8.65(1H, d, J=1.7Hz) | 3.15–3.49(2H, m) |
| 8.37(1H, d, J=8.9Hz) | 2.42–2.64(2H, m) |

Reference Example 9

Preparation of 1-formyl-6-cyano-2-naphthol:

65 milliliters of acetic acid was added to 20 g of 6-cyano-2-naphthol, 3.6 g of paraformaldehyde and 16.6 g of hexamethylenetetramine, followed by stirring at 80° C. for 4 hours. Furthermore, to the reaction mixture was added a solution comprising 53 ml of acetic acid, 10.5 ml of water and 17.8 g of concentrated sulfuric acid at 60° C., followed by stirring at 80° C. for 4 hours. After cooling, 95 ml of water was added to the resulting solution, followed by stirring, and the precipitate was collected by filtration and washed with 40 ml of warm water. To the collected precipitate was added 350 ml of chloroform, followed by refluxing for 1 hour. Thereafter, the precipitate was filtered and the filtrate was concentrated under reduced pressure to obtain a crude product. This product was subjected to silica gel column chromatography using chloroform as an eluent, and the desired fractions were collected, and the solvent was distilled off under reduced pressure. To the residue was added 100 ml of n-hexane and the mixture was stirred for a while, and the precipitate was collected by filtration to obtain 11.2 g of the desired product.

$^1$H-NMR (DMSO-d$_6$) δ ppm:

| | |
|---|---|
| 13.33(1H, S) | 8.03(1H, d, J=8.9Hz) |
| 10.80(1H, S) | |
| 7.78(1H, dd, J1=8.9, J2=1.7Hz) | |
| 8.44(1H, d, J=8.9Hz) | 7.28(1H, d, J=8.9Hz) |
| 8.18(1H, d, J=1.7Hz) | |

Reference Example 10

Preparation of 6-cyano-1-(2-ethoxycarbonylvinyl)-2-naphthol:

A solution prepared by dissolving 19.3 g of 1-formyl-6-cyano-2-naphthol and 42.1 g of ethoxycarbonylmethyltriphenylphosphonium bromide in 140 ml of DMF was added dropwise to a solution comprising 13.6 g of anhydrous potassium carbonate and 250 ml of anhydrous methanol, followed by stirring for 3 hours under cooling with ice in a nitrogen stream and 24 hours at room temperature. The precipitate was filtered, and 2.7 liters of water was added to the filtrate, followed by stirring for 2 hours. Then, the precipitate was collected by filtration and washed with 90 ml of methanol to obtain 12.6 g of the desired product.

$^1$H-NMR (DMSO-d$_6$) δ ppm:

| | |
|---|---|
| 11.38(1H, brs) | 8.46(1H, d, J=1.7Hz) |
| 8.09–8.30(2H, m) | 7.98(1H, d, J=8.9Hz) |
| 7.77(1H, dd, J1=8.9, J2=1.7Hz) | |
| 7.40(1H, d, J=8.9Hz) | 6.84(1H, d, J=15.8Hz) |
| 4.24(2H, q, J=7.3Hz) | 1.31(3H, t, J=7.3Hz) |

Reference Example 11

Preparation of 6-cyano-1-(2-carbamoylvinyl)-2-naphthol:

2.0 Liters of 25% aqueous ammonia was added to 25.2 g of 6-cyano-1-(2-ethoxycarbonylvinyl)-2-naphthol, followed by stirring at 40°–45° C. for 32 hours. After cooling, the reaction mixture was concentrated to 300 ml under reduced pressure, and the residue was stirred for 30 minutes under cooling with water. The precipitate was collected by filtration and washed with a small amount of water and acetone to obtain 9.55 g of the desired product.

$^1$H-NMR (DMSO-d$_6$) δ ppm:

| | |
|---|---|
| 8.46(1H, d, J=1.7Hz) | 8.22(1H, d, J=8.9Hz) |
| 7.87–8.07(2H, m) | |
| 7.77(1H, dd, J1=8.9, J2=1.7Hz) | |
| 7.70(1H, S) | 7.40(1H, d, J=8.9Hz) |
| 7.16(1H, S) | 6.94(1H, d, J=15.8Hz) |

EXAMPLE 45

Preparation of 6-amidino-1-(2-carbamoylvinyl)-2-naphthol.hydrochloride:

9.0 Grams of 6-cyano-1-(2-carbamoylvinyl)-2-naphthol was added to 750 ml of anhydrous methanol solution saturated with dry hydrogen chloride gas, followed by stirring for 72 hours under cooling with ice. The precipitate was collected by filtration and washed with small amounts of ether and acetone. This collected precipitate was added to 900 ml of anhydrous methanol solution saturated with dry ammonia gas, followed by stirring for 120 hours at room temperature. The precipitate was collected by filtration and washed with a small amount of methanol. To this collected precipitate was added 35 ml of DMF, and 15 g of 25% hydrochloric acid was added to the resulting solution, followed by stirring for 30 minutes under cooling with ice. Furthermore, to this solution was added 200 ml of acetone, followed by stirring for 30 minutes under cooling with ice. The precipitate was collected by filtration and washed with small amounts of ether and acetone to obtain 5.5 g of the desired product.

$^1$H-NMR (DMSO-d$_6$) δ ppm:

| | |
|---|---|
| 9.53(2H, S) | 7.96(1H, d, J=8.9Hz) |
| 9.30(2H, S) | |
| 7.90(1H, dd, J1=8.9, J2=1.7Hz) | |
| 8.50(1H, dd, J=1.7Hz) | 7.58(1H, d, J=8.9Hz) |
| 8.26(1H, d, J=8.9Hz) | 6.99(1H, d, J=15.8Hz) |
| 8.02(1H, d, J=15.8Hz) | |

EXAMPLE 46

Preparation of 6-amidino-1-(2-carbamoylvinyl)-2-naphthyl 4-aminoiminomethylaminobenzoate.dihydrochloride:

90 Milliliters of 20% hydrous pyridine was added to 5.08 g of 4-aminoiminomethylaminobenzoic acid.methanesulfonate, 4.5 g of 6-amidino-1-(2-carbamoylvinyl)-2-naphthol.hydrochloride, 6.34 g of DCC and 80 mg of DMAP, followed by stirring for 2 hours under cooling with ice and then 48 hours at room temperature. Then, the precipitate was collected by filtration and washed twice with 160 ml of warm 20% hydrous pyridine. The above-obtained reaction filtrate and the warm hydrous pyridine wash liquid were combined and the resulting solution was added to 1 liter of acetone, followed by stirring for 24 hours under cooling with ice. The precipitate was collected by filtration and thereto was added 70 ml of warm DMF to dissolve the precipitate. Then, 0.5 g of active carbon was added, followed by stirring for 30 minutes at room temperature. Insoluble matter was filtered and 8.4 ml of concentrated hydrochloric acid was added to the filtrate. The resulting solution was added dropwise to 600 ml of acetone, followed by stirring for 24 hours under cooling with ice. Then, the precipitate was collected by filtration to obtain 6.8 g of the desired product.

$^1$H-NMR (DMSO-$d_6$) δ ppm:

| | |
|---|---|
| 10.78(1H, S) | 7.90–8.14(5H, m) |
| 9.71(2H, S) | 7.88(1H, S) |
| 9.46(2H, S) | 7.76(1H, d, J=15.8Hz) |
| 8.70(1H, d, J=1.7Hz) | 7.70(1H, d, J=8.9Hz) |
| 8.28(1H, d, J=8.9Hz) | 7.48(2H, d, J=8.6Hz) |
| 8.23(2H, d, J=8.6Hz) | 7.28(1H, S) |
| 8.22(1H, d, J=8.9Hz) | 6.65(1H, d, J=15.8Hz) |

Reference Example 12

Preparation of 6-cyano-1-dimethylcarbamoylmethoxycarbonyl-2-naphthol:

To 28.4 g of 6-cyano-1-carboxy-2-naphthol were added 350 ml of acetonitrile, 18 ml of triethylamine and 33.2 g of dimethylcarbamoylmethyl bromide, followed by stirring for 24 hours at 70° C. and further 24 hours at room temperature. The resulting precipitate was collected by filtration and washed with water to obtain 31.2 g of the desired product.

$^1$H-NMR (DMSO-$d_6$) δ ppm:

| | |
|---|---|
| 11.27(1H, S) | 7.36(1H, d, J=8.9Hz) |
| 8.52(1H, S) | 5.23(2H, S) |
| 8.37(1H, d, J=8.9Hz) | 3.04(3H, S) |
| 8.10(1H, d, J=8.9Hz) | 2.95(3H, S) |
| 7.80(1H, dd, J1=8.9, J2=1.7Hz) | |

EXAMPLE 47

Preparation of 6-amidino-1-dimethylcarbamoylmethoxycarbonyl-2-naphthol.hydrochloride:

600 Milliliters of anhydrous methanol was added to 29.8 g of 6-cyano-1-dimethylcarbamoylmethoxycarbonyl-2-naphthol, and dry hydrogen chloride gas was passed through the solution under cooling with ice and stirring to saturate the solution with hydrogen chloride gas, followed by further stirring for 24 hours under cooling with water. The reaction mixture was added dropwise to 3.0 liters of anhydrous methanol, followed by stirring for 1 hour under cooling with ice and the precipitate was collected by filtration. This was added to a solution prepared by passing dry ammonia gas through 240 ml of anhydrous methanol under cooling with ice and stirring to saturate the methanol with the gas, followed by stirring for 96 hours under cooling with water. The precipitate was collected by filtration and washed with 150 ml of methanol, 100 ml of water and 100 ml of acetone. To this collected precipitate was added 100 ml of a methanol solution saturated with dry hydrogen chloride gas, followed by stirring for 2 hours under cooling with ice. The precipitate was collected by filtration and washed with a small amount of diisopropyl ether to obtain a crude product. This was dissolved in 1.2 liter of 50% hydrous methanol and 10 g of active carbon was added thereto, followed by stirring for 1 hour at room temperature. Insoluble matter was filtered off and the filtrate was concentrated to 200 ml under reduced pressure. Then, the precipitate was collected by filtration and washed with small amounts of cold methanol and acetone to obtain 18.7 g of the desired product.

$^1$H-NMR (DMSO-$d_6$) δ ppm:

| | |
|---|---|
| 11.33(1H, S) | |
| 7.89(1H, dd, J=8.9, J2=1.7Hz) | |
| 9.53(2H, S) | 7.44(1H, d, J=8.9Hz) |
| 9.33(2H, S) | 5.22(2H, S) |
| 8.52(1H, d, J=1.7Hz) | 3.04(3H, S) |
| 8.43(1H, d, J=8.9Hz) | 2.94(3H, S) |
| 8.11(1H, d, J=8.9Hz) | |

EXAMPLE 48

Preparation of 6-amidino-1-dimethylcarbamoylmethoxycarbonyl-2-naphthyl 4-[(4,5-dihydro-1H-imidazol-2-yl)amino]benzoate.dihydrochloride:

15 Milliliters of anhydrous pyridine was added to 1.0 g of 4-[(4,5-dihydro-1H-imidazol-2-yl)amino]-benzoic acid.hydrochloride, 1.38 g of 6-amidino-1-dimethylcarbamoylmethoxycarbonyl-2-naphthol.hydrochloride, 1.28 g of DCC and 50.5 mg of DMAP, followed by stirring for 2 hours under cooling with ice and then 48 hours at room temperature. Then, the precipitate was collected by filtration, and dissolved by adding thereto 50 ml of warm DMF, 0.5 ml of 1N-hydrochloric acid and 2 ml of water, followed by stirring for 1 hour under cooling with ice. The precipitate was filtered and the filtrate was concentrated under reduced pressure. To the residue was added 15 ml of DMF, and the solution was added dropwise to a mixed liquid of 150 ml of acetone and 50 ml of ether, followed by stirring for 1 hour under cooling with ice. Then, the precipitate was collected by filtration to obtain a crude product. Then, the product was subjected to silica gel column chromatography using methyl ethyl ketone-water-acetic acid (80:15:5) as an eluent, and the desired fractions were collected and the solvent was distilled off under reduced pressure. To the residue were added 5 ml of DMF and 0.7 ml of concentrated hydrochloric acid, and the solution was added dropwise to 150 ml of acetone, followed by stirring for 24 hours under cooling with ice. Then, the precipitate was collected by filtration to obtain 447.8 mg of the desired product.

$^1$H-NMR (DMSO-$d_6$) δ ppm:

| | |
|---|---|
| 11.83(1H, brs) | |
| 8.07(1H, dd, J1=8.9, J2=1.7Hz) | |
| 9.81(2H, S) | 7.79(1H, d, J=8.9Hz) |
| 9.61(2H, S) | 7.54(2H, d, J=8.6Hz) |
| 8.85(2H, S) | 5.12(2H, S) |
| 8.84(1H, d, J=8.9Hz) | 3.73(4H, S) |
| 8.78(1H, d, J=1.7Hz) | 2.97(3H, S) |

| | |
|---|---|
| 8.38(1H, d, J=8.9Hz) | 2.89(3H, S) |
| 8.16(2H, d, J=8.6Hz) | |

EXAMPLE 49

Preparation of 6-amidino-1-dimethylcarbamoylmethoxycarbonyl-2-naphthyl 4-aminoiminomethylaminobenzoate.dimethanesulfonate:

3 Milliliters of anhydrous pyridine was added to 418 mg of 4-aminoiminomethylaminobenzoic acid.methanesulfonate, 500 mg of 6-amidino-1-dimethylcarbamoylmethoxycarbonyl-2-naphthol.hydrochloride, 400 mg of DCC and 18 mg of DMAP, followed by stirring for 2 hours under cooling with ice and then 24 hours at room temperature. Then, the precipitate was collected by filtration and dissolved with addition of 20 ml of warm DMF, followed by stirring for 1 hour under cooling with ice. The precipitate was filtered and the filtrate was added dropwise to 400 ml of ether, followed by stirring for 24 hours under cooling with ice. The precipitate was collected by filtration and dissolved with addition of 20 ml of water, and the solution was added dropwise to 100 ml of aqueous sodium bicarbonate solution, followed by stirring for 2 hours under cooling with ice. Then, the precipitate was collected by filtration and washed with small amounts of water and acetone. This was added to a solution comprising 20 ml of DMF and 0.36 ml of methanesulfonic acid. The resulting solution was added dropwise to 450 ml of acetone, followed by stirring for 24 hours under cooling with ice. Then, the precipitate was collected by filtration to obtain 312.5 mg of the desired product.

$^1$H-NMR (DMSO-$d_6$) δ ppm:

| | |
|---|---|
| 10.27(1H, S) | 7.89(4H, S) |
| 9.53(2H, S) | 7.79(1H, d, J=8.9Hz) |
| 9.27(2H, S) | 7.46(2H, d, J=8.6Hz) |
| 8.86(1H, d, J=8.9Hz) | 5.11(2H, S) |
| 8.66(1H, d, J=1.7Hz) | 2.96(3H, S) |
| 8.42(1H, d, J=8.9Hz) | 2.89(3H, S) |
| 8.17(2H, d, J=8.6Hz) | 2.42(6H, S) |
| 7.99(1H, dd, J1=8.9, J2=1.7Hz) | |

EXAMPLE 50

Preparation of 6-amidino-1-(2-ethoxycarbonylethyl)-2-naphthol.hydrochloride:

600 Milliliters of 3.6% hydrochloric acid was added to 3.6 g of 6-amidino-1-(2-carbamoylethyl)-2-naphthol.hydrochloride, followed by stirring at 90° C. for 6 hours. The reaction mixture was concentrated under reduced pressure, and to the residue was added 100 ml of ethanol, followed by stirring for 1 hour. Insoluble matter was filtered off, and the filtrate was concentrated under reduced pressure. To the residue was added 200 ml of anhydrous methanol. Dry hydrogen chloride gas was passed through the solution under cooling with ice and stirring to saturate the solution with the dry hydrogen chloride gas, followed by stirring for 24 hours under cooling with water. A small amount of insoluble matter was filtered off and the filtrate was concentrated under reduced pressure. To the residue was added 60 ml of water to dissolve the residue. The resulting solution was added dropwise to 140 ml of saturated aqueous sodium bicarbonate solution, followed by stirring for 30 minutes under cooling with ice. After the supernatant was decanted, a small amount of water was added to the residue and the supernatant was decanted. To the residue were added 10 ml of ethanol and 5 ml of acetone and, further, 4.3 ml of concentrated hydrochloric acid to dissolve the residue. This solution was added dropwise to 700 ml of ether, followed by stirring for 2 hours under cooling with ice. The supernatant was decanted, and to the residue were added 40 ml of acetone and 200 ml of ether, followed by stirring for 1 hour. Then, the precipitate was collected by filtration to obtain 1.64 g of the desired product.

$^1$H-NMR (DMSO-$d_6$) δ ppm:

| | |
|---|---|
| 10.50(1H, S) | 7.44(1H, d, J=8.9Hz) |
| 9.46(2H, S) | 4.05(2H, q, J=7.3Hz) |
| 9.25(2H, S) | 3.16–3.37(2H, m) |
| 8.46(1H, d, J=1.7Hz) | 2.39–2.64(2H, m) |
| 8.07(1H, d, J=8.9Hz) | 1.15(3H, t, J=7.3Hz) |
| 7.74–7.92(2H, m) | |

EXAMPLE 51

Preparation of 6-amidino-1-(2-ethoxycarbonylethyl)-2-naphthyl 4-[(4,5-dihydro-1H-imidazol-2-yl)amino]benzoate.dihydrochloride:

30 Milliliters of 20% hydrous pyridine was added to 1.12 g of 4-[(4,5-dihydro-1H-imidazol-2-yl)amino]benzoic acid.hydrochloride, 1.5 g of 6-amidino-1-(2-ethoxycarbonylethyl)-2-naphthol.hydrochloride, 1.44 g of DCC and 56.7 mg of DMAP, followed by stirring for 2 hours under cooling with ice and then 48 hours at room temperature. Furthermore, 1.44 g of DCC, 5 ml of 20% hydrous pyridine and 10 ml of DMF were added, followed by stirring for 24 hours at room temperature. Then, the precipitate was filtered and the filtrate was concentrated rated under reduced pressure. To the residue was added 20 ml of DMF, and the resulting solution was added dropwise to 400 ml of ether, followed by stirring for 24 hours under cooling with ice. The supernatant was decanted to obtain a crude product. This was subjected to silica gel column chromatography using methyl ethyl ketone-water-acetic acid (80:15:5) as an eluent, and the desired fractions were collected and the solvent was distilled off under reduced pressure. To the residue were added 10 ml of ethanol and 1.55 ml of concentrated hydrochloric acid, followed by stirring for 1 hour under cooling with ice. Then, the precipitate was collected by filtration to obtain 307.9 mg of the desired product.

$^1$H-NMR (DMSO-$d_6$) δ ppm:

| | |
|---|---|
| 11.71(1H, S) | 8.09(1H, d, J=8.9Hz) |
| 9.70(2H, S) | |
| 8.01(1H, dd, J1=8.9, J2=1.7Hz) | |
| 9.50(2H, S) | 7.62(1H, d, J=8.9Hz) |
| 8.79(2H, S) | 7.55(2H, d, J=8.6Hz) |
| 8.67(1H, d, J=1.7Hz) | 3.98(2H, q, J=6.9Hz) |
| 8.36(1H, d, J=8.9Hz) | 3.74(4H, S) |
| 8.25(2H, d, J=8.6Hz) | 1.06(3H, t, J=6.9Hz) |

Formulation Example 1

| | |
|---|---|
| The present compound | 100 mg |
| Lactose | 30 mg |
| Avicel | 30 mg |
| Carboxycellulose | 20 mg |
| Succinic acid | 18 mg |
| Magnesium stearate | 2 mg |

The above components (200 mg in total) are filled into a capsule or tableted.

Formulation Example 2

| The present compound | 100 mg |
|---|---|
| Lactose | 50 mg |
| Avicel | 20 mg |
| Carboxycellulose | 20 mg |
| Succinic acid | 8 mg |
| Magnesium stearate | 2 mg |

The above components (200 mg in total) are filled into a capsule or tableted.

Formulation Example 3

| The present compound | 100 mg |
|---|---|
| Lactose | 45 mg |
| Corn starch | 27 mg |
| Low-substitution hydroxypropylcellulose | 27 mg |
| Magnesium stearate | 1 mg |

The above components (200 mg in total) are filled into a capsule or tableted.

Formulation Example 4

| The present compound | 0.2 g |
|---|---|
| Witepsol | 1.1 g |

The above components were formulated into a suppository by a conventional method.

Effects of the Invention

The present compound which can be orally administered has fibrinolysis promoting action and exhibits excellent thrombolytic activity and, therefore, is effective for treatment of diseases caused by thrombus. That is, it can be used as medicines for general thrombosis and embolism, for example, medicines for treatment of thrombosis and embolism such as venous thrombosis, myocardial infarction, pulmonary occlusion, cerebral embolism, slowly advancing cerebral thrombosis, and thrombosis and embolism caused by operation of blood vessels and extracorporeal circulation, and improvement of obstruction of blood stream, improvement of various diseases caused by chronic artery occlusion, and treatment of thrombosis and embolism caused by ischemic cerebral artery injuries.

It has been proved by the following experiments that the present compounds have fibrinolysis promoting action and exhibit excellent thrombus-resolving action and, therefore, are effective for treatment of various diseases caused by thrombus.

(1) Preventive effect on death due to pulmonary thrombosis of mouse models:

For experiment, ddy male mice after a fast of 6 hours were used and 10 mg/kg of the present compound was orally administered. For positive control group, was administered Sepimostat mesilate which exhibits thrombolytic activity for human through oral administration. After lapse of 6 hours, 10 units/mouse of thrombin was administered to the mice through caudal vein to cause thrombosis for the mice. After 16 hours from thrombin-induction, mortality was checked and the preventive effect on death (survival rate) was indicated by the ratio to the survival rate of the positive control group. The results are shown in Table 1.

TABLE 1

| Compound | Preventive effect on death |
|---|---|
| Example 1 | 1.16 |
| Example 3 | 1.09 |
| Example 5 | 1.00 |
| Example 7 | 1.05 |
| Example 11 | 1.12 |
| Example 12 | 1.05 |
| Example 15 | 1.05 |
| Example 31 | 1.00 |
| Example 39 | 1.19 |
| Example 48 | 0.96 |

The above results show that the present compounds have the effect equal to the control compound having excellent thrombus-resolving action.

(2) Test of determination of blood plasmin like activity using synthetic substrate:

For the test, SD male rats (8 weeks old) after fasted overnight were used, and 100 mg/kg of the present compound was orally administered to the rats, and blood was drawn, with time, from the descending aorta as citrate-containing blood and subjected to centrifugation to obtain plasma. Water was orally administered to the rats of control group and plasma was similarly obtained.

To the plasma obtained were added 0.1M borate buffer solution (pH 8.5) and Boc-Val-Leu-Lys-MCA and incubation was conducted at 37° C. for 30 minutes. Thereto was added 15% acetic acid to terminate the reaction, and thereafter, fluorescence intensity was measured to determine plasmin like activity to find that the present compound showed increase of blood plasmin like activity. The results are shown in Table 2.

TABLE 2

| Compound | Plasmin like activity (nmol/min/ml) |
|---|---|
| Example 1 | 0.37 |
| Example 7 | 0.62 |
| Example 17 | 0.62 |
| Example 24 | 0.55 |
| Example 26 | 0.60 |
| Example 27 | 0.52 |
| Example 39 | 0.58 |
| Example 46 | 0.63 |
| Water | 0.07 |

The above results clearly show that the present compounds exhibit thrombolytic activity.

(3) Test of measurement of plasminogen activator inhibitor (PAI-1) antigen quantity:

Measurement of PAI-1 antigen quantity was conducted using the plasma obtained in the above Test (2).

Previously, 100 µl of a diluted 10 mM carbonate buffered solution of monoclonal antibody to PAI-1 was put in each well of a 96-well micro-titer plate and left to stand for 16 hours at 4° C., followed by washing, four times, with 10 mM phosphate buffer solution containing 0.1% Tween 20 and adding a standard solution and the plasma sample. After leaving for 2 hours at room temperature and washing again four times, 100 µl of an enzyme-labelled PAI-1 polyclonal antibody was added to carry out reaction at room temperature for 2 hours. After excess antibody was washed, 100 µl of citric acid buffer solution containing 10 mg of o-phenylenediamine and 0.1% hydrogen peroxide was added, followed by leaving it for 30 minutes at 30° C. to cause color formation. After the reaction was terminated by the addition of 50 μl of 2N sulfuric acid, absorbance at 405 nm was measured by a micro-plate reader to determine the PAI-1 antigen quantity in the plasma sample. The results are shown in Table 3.

TABLE 3

| Compound | PAI-1 antigen quantity (ng/ml) |
|---|---|
| Example 1 | 28.5 |
| Water | 54.2 |

In the control mechanism of thrombolysis, most of t-PA released into plasma is rapidly inhibited by PAI-1 which is the specific inhibitor and loses activity. Therefore, decrease of quantity of PAI-1 results in promotion of thrombus-resolving action. In the group treated with the present compound, the blood PAI-1 antigen quantity was clearly reduced.

By the way, it is recognized that the toxicity of the present compounds is very low and administration of them to human and mammals cause no problem.

We claim:

1. A compound represented by the formula (I) or pharmaceutically acceptable acid addition salts thereof:

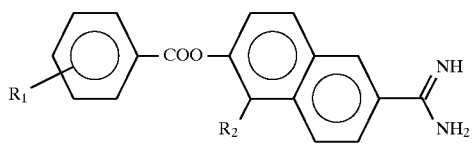

wherein $R_1$ represents (4,5-dihydro-1H-imidazol-2-yl) amino group, (4,5-dihydro-1,3-thiazol-2-yl)amino group, amidino group, morpholinomethyl group, nitro group, amino group, dimethylamino group,

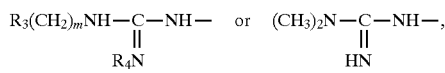

$R_3$ represents hydrogen, methoxy group, hydroxyl group, acetylamino group, morpholino group, piperidino group, 1-pyrrolidinyl group or dimethylamino group, m represents 0–4, $R_4$ represents hydrogen or methyl group, $R_2$ represents $NH_2CO(CH_2)_n-$, 2-(carbamoyl)vinyl group or $R_5OOC(CH_2)_n-$, $R_5$ represents dimethylcarbamoylmethyl group, hydrogen or lower alkyl group, and n represents 0–2.

2. A compound according to claim 1 which is represented by the formula (V) or phamaceutically acceptable acid addition salts thereof:

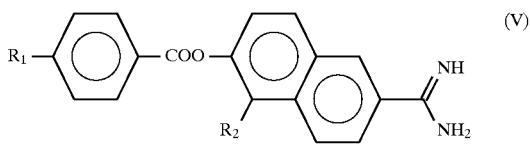

wherein $R_1$ represents (4,5-dihydro-1H-imidazol-2-yl) amino group, $R_2$ represents $NH_2CO(CH_2)_n-$, and n represents 0–2.

3. A pharmaceutical formulation which contains the compound of claim 1 together with at least one pharmaceutically acceptable carrier.

4. A pharmaceutical formulation according to claim 3 which is a fibrinolysis promoter.

5. A compound represented by the formula (II):

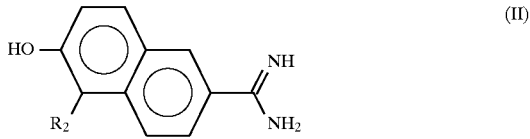

wherein $R_2$ represents $NH_2CO(CH_2)_n-$, 2-(carbamoyl) vinyl group or $R_5OOC(CH_2)_n-$, $R_5$ represents dimethylcarbamoylmethyl group, hydrogen or lower alkyl group, and n represents 0–2, wherein n cannot equal 0 if $R_5=CH_3$.

6. A pharmaceutical formulation which contains the compound of claim 2 together with at least one pharmaceutically acceptable carrier.

7. A method for treating thrombotic conditions in humans and mammals, which comprises administering to a human or mammal in need thereof an effective amount of the compound defined in claim 1.

8. A method for treating thrombotic conditions in humans and mammals, which comprises administering to a human or mammal in need thereof an effective amount of the compound defined in claim 2.

9. A method for lysis of thrombus in humans or mammals, which comprises administering to a human or mammal in need thereof an effective amount of the compound defined in claim 1.

10. A method for lysis of thrombus in humans or mammals, which comprises administering to a human or mammal in need thereof an effective amount of the compound defined in claim 2.

11. A method of promoting fibrinolysis action in humans or mammals, which comprises administering to a human or mammal in need thereof an effective amount of the compound defined in claim 1.

12. A method of promoting fibrinolysis action in humans or mammals, which comprises administering to a human or mammal in need thereof an effective amount of the compound defined in claim 2.

* * * * *